United States Patent
Kania et al.

(10) Patent No.: US 12,358,897 B2
(45) Date of Patent: Jul. 15, 2025

(54) COMPOUNDS AND METHOD OF TREATING COVID-19

(71) Applicant: Pfizer Inc., New York, NY (US)

(72) Inventors: Robert Steven Kania, Del Mar, CA (US); Dafydd Rhys Owen, Concord, MA (US); Martin Youngjin Pettersson, Littleton, MA (US); Matthew Forrest Sammons, Qunicy, MA (US); Jamison Bryce Tuttle, Marblehead, MA (US)

(73) Assignee: Pfizer Inc., New York, NY (US)

( * ) Notice: Subject to any disclaimer, the term of this patent is extended or adjusted under 35 U.S.C. 154(b) by 457 days.

(21) Appl. No.: 17/906,132

(22) PCT Filed: Mar. 31, 2021

(86) PCT No.: PCT/IB2021/052689
§ 371 (c)(1),
(2) Date: Sep. 12, 2022

(87) PCT Pub. No.: WO2021/205290
PCT Pub. Date: Oct. 14, 2021

(65) Prior Publication Data
US 2023/0120707 A1    Apr. 20, 2023

Related U.S. Application Data

(60) Provisional application No. 63/159,083, filed on Mar. 10, 2021, provisional application No. 63/005,378, filed on Apr. 5, 2020.

(51) Int. Cl.
*C07D 403/14*    (2006.01)
*A61K 9/00*    (2006.01)
*A61K 9/20*    (2006.01)

(52) U.S. Cl.
CPC .......... *C07D 403/14* (2013.01); *A61K 9/0056* (2013.01); *A61K 9/0073* (2013.01); *A61K 9/20* (2013.01)

(58) Field of Classification Search
CPC .. C07D 403/14; A61K 9/0056; A61K 9/0073; A61K 9/20
USPC ...................................................... 514/414
See application file for complete search history.

(56) References Cited

FOREIGN PATENT DOCUMENTS

WO    2005113580    12/2005
WO    2021/205290 A1    10/2021

OTHER PUBLICATIONS

Hoffman, Robert L., et al., "Discovery of Ketone-Bse Covalent Inhibitors of Coronavirus 3CL Proteases for the Potential Therapeutic Treatment of COVID-19", Journal of Medicinal Chemistry, Nov. 12, 2020, pp. 12725-12747, 63(21).
International Search Report and Written Opinion, PCT/IB2021/052689, filed Mar. 31, 2021, mailed Jun. 24, 2021, 15 pages.
Zhang, Linlin, et al., "Crystal structure of SARS-COV-2 main protease provides a basis for design of improved [alpha]—ketoamide inhibitors", Science, Mar. 20, 2020, pp. 409-412, 368(6489).
International Preliminary Report on Patentability issued in PCT/IB2021/052689; mailed on Oct. 20, 2022; 7 pp.
International Search Report issued in PCT/IB2021/052689; mailed on Jun. 24, 2021; 5 pp.
Written Opinion issued in PCT/IB2021/052689; mailed on Jun. 24, 2021; 5 pp.

*Primary Examiner* — Kristin A Vajda
(74) *Attorney, Agent, or Firm* — John A. Wichtowski

(57) ABSTRACT

The invention relates to compounds of formula I

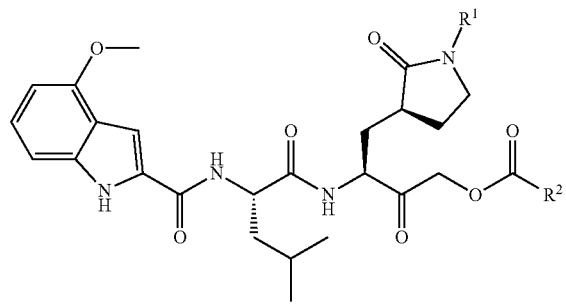

wherein $R^1$ and $R^2$ are as defined herein, pharmaceutical compositions comprising the compounds and methods of treating COVID-19 in a patient by administering therapeutically effective amounts of the compounds and methods of inhibiting or preventing replication of SARS-COV-2 with the compound.

23 Claims, 2 Drawing Sheets
Specification includes a Sequence Listing.

COMPOUNDS AND METHOD OF TREATING COVID-19

This application is a national stage application under 35 U.S.C. 371 of PCT/IB2021/052689, filed on Mar. 31, 2021, which claims the benefit of U.S. Provisional Patent Application No. 63/159,083, filed on Mar. 10, 2021, and U.S. Provisional Patent Application No. 63/005,378, filed on Apr. 5, 2020, the disclosures of which are hereby incorporated by reference in their entirety.

This application is being filed electronically via EFS-Web and includes an electronically submitted sequence listing in .txt format. The .txt file contains a sequence listing entitled "PC072621A-SARS-COVID-Cov 3CL-SARS-Cov-2 3CL_ST25.txt" created on Jul. 22, 2022 and 6 KB in size. The sequence listing contained in this .txt file is part of the specification and is herein incorporated by reference in its entirety.

BACKGROUND OF THE INVENTION

The invention relates to compounds and methods of inhibiting viral replication activity comprising contacting a SARS-Cov-2-related 3C-like ("3CL") proteinase with a therapeutically effective amount of a SARS-Cov-2-related 3C-like protease inhibitor. The invention also relates to methods of treating Coronavirus Disease 2019 ("COVID-19") in a patient by administering a therapeutically effective amount of a SARS-Cov-2-related 3C-like protease inhibitor to a patient in need thereof. The invention further relates to methods of treating COVID-19 in a patient, the method comprising administering a pharmaceutical composition comprising a therapeutically effective amount of the SARS-Cov-2-related 3C-like protease inhibitor to a patient in need thereof.

A worldwide outbreak of Coronavirus Disease 2019 ("COVID-19") has been associated with exposures originating in late 2019 in Wuhan, Hubei Province, China. By early April 2020 the outbreak of COVID-19 has evolved into a global pandemic with over one million people having been confirmed as infected and resulting in over 50,000 deaths. By March 2021 over 115 million people have been infected globally with over 2.5 million people having died as a result of this disease. The causative agent for COVID-19 has been identified as a novel coronavirus which has been named Severe Acute Respiratory Syndrome Corona Virus 2 ("SARS-CoV-2"). The genome sequence of SARS-CoV-2 has been sequenced from isolates obtained from nine patients in Wuhan, China and has been found to be of the subgenus Sarbecovirus of the genus Betacoronovirus. Lu, R. et al. The Lancet, Jan. 29, 2020; http://doi.org/10.1016/S0140-6736(20). The sequence of SARS-CoV-2 was found to have 88% homology with two bat-derived SARS-like coronaviruses, bat-SL-CoVZC45 and bat-SL-CoVZXC21 which were collected in 2018 in Zhoushan, eastern China. SARS-CoV-2 was also found to share about 79% homology with Severe Acute Respiratory Syndrome Corona Virus ("SARS-CoV"), the causative agent of the SARS outbreak in 2002-2003, and about 50% homology with Middle East Respiratory Syndrome Coronavirus ("MERS-CoV"), the causative agent of a respiratory viral outbreak originating in the Middle East in 2012. Based on a recent analysis of 103 sequenced genomes of SARS-CoV-2 it has been proposed that SARS-CoV-2 can be divided into two major types (L and S types) with the S type being ancestral and the L type having evolved from the S-type. Lu, J.; Cui, J. et al. On the origin and continuing evolution of SARS-CoV-2; http://doi.org/10.1093/nsr/nwaa036. The S and L types can be clearly defined by just two tightly linked SNPs at positions 8,782 (orf1ab:T8517C, synonymous) and 28,144 (ORFS: C251T, S84L). In the 103 genomes analyzed approximately 70% were of the L-type and approximately 30% were of the S-type. It is unclear if the evolution of the L-type from the S-type occurred in humans or through a zoonotic intermediate but it appears that the L-type is more aggressive than the S-type and human interference in attempting to contain the outbreak may have shifted the relative abundance of the L and S types soon after the SARS-CoV-2 outbreak began. The discovery of the proposed S- and L-subtypes of SARS-CoV-2 raises the possibility that an individual could potentially be infected sequentially with the individual subtypes or be infected with both subtypes at the same time. In view of this evolving threat there is an acute need in the art for an effective treatment for COVID-19 and for methods of inhibiting replication of the SARS-CoV-2 coronavirus.

Recent evidence clearly shows that the newly emerged coronavirus SARS-CoV-2, the causative agent of COVID-19 (Centers for Disease Control, CDC) has acquired the ability of human to human transmission leading to community spread of the virus. The sequence of the SARS-CoV-2 receptor binding domain ("RBD"), including its receptor-binding motif (RBM) that directly contacts the angiotensin 2 receptor, ACE2, is similar to the RBD and RBM of SARS-CoV, strongly suggesting that SARS-CoV-2 uses ACE2 as its receptor. Yushun Wan, Y.; Shang, J.; Graham, R.; 2, Baric, R. S.; Li, F.; Receptor recognition by novel coronavirus from Wuhan: An analysis based on decade-long structural studies of SARS; J. Virol. 2020; doi:10.1128/JVI.00127-20. Several critical residues in SARS-CoV-2 RBM (particularly $Gln^{493}$) provide favorable interactions with human ACE2, consistent with SARS-CoV-2's capacity for human cell infection. Several other critical residues in SARS-CoV-2's RBM (particularly $Asn^{501}$) are compatible with, but not ideal for, binding human ACE2, suggesting that SARS-CoV-2 uses ACE2 binding in some capacity for human-to-human transmission.

Coronavirus replication and transcription function is encoded by the so-called "replicase" gene (Ziebuhr, J., Snijder, E. J., and Gorbaleya, A. E.; Virus-encoded proteinases and proteolytic processing in Nidovirales. J. Gen. Virol. 2000, 81, 853-879; and Fehr, A. R.; Perlman, S.; Coronaviruses: An Overview of Their Replication and Pathogenesis Methods Mol Biol. 2015; 1282: 1-23. doi: 10.1007/978-1-4939-2438-7_1), which consists of two overlapping polyproteins that are extensively processed by viral proteases. The C-proximal region is processed at eleven conserved interdomain junctions by the coronavirus main or "3C-like" protease (Ziebuhr, Snijder, Gorbaleya, 2000 and Fehr, Perlman et al., 2015). The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. The SARS-CoV-2 3CL protease sequence (Accession No. YP_009725301.1) has been found to share 96.08% homology when compared with the SARS-CoV 3CL protease (Accession No. YP_009725301.1) Xu, J.; Zhao, S.; Teng, T.; Abdalla, A. E.; Zhu, W.; Xie, L.; Wang, Y.; Guo, X.; Systematic Comparison of Two Animal-to-Human Transmitted Human Coronaviruses: SARS-CoV-2 and SARS-CoV; Viruses 2020, 12, 244; doi:10.3390/v12020244. Very recently Hilgenfeld and colleagues published a high-resolution X-ray structure of the SARS-CoV-2 coronavirus main protease (3CL) Zhang, L.;

Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879. The structure indicates that there are differences when comparing the 3CL proteases of SARS-CoV-2 and SARS-CoV. In the SARS-CoV but not in the SARS-CoV-2 3CL protease dimer, there is a polar interaction between the two domains III involving a 2.60-Å hydrogen bond between the side-chain hydroxyl groups of residue Thr$^{285}$ of each protomer, and supported by a hydrophobic contact between the side-chain of Ile$^{286}$ and Thr$^{285}$ Cγ$_2$. In the SARS-CoV-2 3CL, the threonine is replaced by alanine, and the isoleucine by leucine when compared with the same residues in the SARS-CoV 3CL. The Thr285Ala replacement observed in the SARS-CoV-2 3CL protease allows the two domains III to approach each other somewhat closer (the distance between the Cα atoms of residues 285 in molecules A and B is 6.77 Å in SARS-CoV 3CL protease and 5.21 Å in SARS-CoV-2 3CL protease and the distance between the centers of mass of the two domains III shrinks from 33.4 Å to 32.1 Å). In the active site of SARS-CoV-2 3CL Cys$^{145}$ and His$^{41}$ form a catalytic dyad which when taken together with a with a buried water molecule that is hydrogen bonded to His$^{41}$ can be considered to constitute a catalytic triad of the SARS-CoV-2 3CL protease. In view of the ongoing SARS-CoV-2 spread which has caused the current worldwide COVID-19 outbreak it is desirable to have new methods of inhibiting SARS-CoV-2 viral replication and of treating COVID-19 in patients.

SUMMARY OF THE INVENTION

The present invention provides novel compounds which act in inhibiting or preventing SARS-Cov-2 viral replication and thus are useful in the treatment of COVID-19. The present invention also provides pharmaceutical compositions comprising the compounds and methods of treating COVID-19 and inhibiting SARS-Cov-2 viral replication by administering the compounds of the invention or pharmaceutical compositions comprising the compounds of the invention.

E1 is a Compound of Formula I

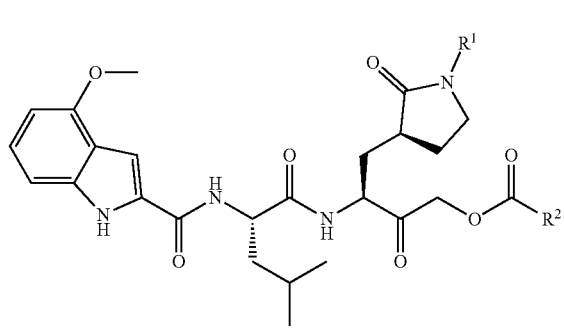

I wherein $R^1$ is selected from the group consisting of hydrogen, —C(O)C$_1$-C$_6$alkyl, —C(O)OC$_1$-C$_6$alkyl and —C$_1$-C$_6$alkylOC(O)OC$_1$-C$_6$alkyl;
when $R^1$ is hydrogen then $R^2$ is selected from the group consisting of ethyl, isopropyl, 2-methylpropyl, C$_1$-C$_6$alkyl substituted with one to three $R^3$, cyclopropyl substituted with one to three $R^4$, C$_4$-C$_7$cycloalkyl unsubstituted or substituted with one to three $R^4$, C$_5$-C$_{12}$bicycloalkyl unsubstituted or substituted with one to three $R^4$, four- to seven-membered heterocycloalkyl comprising one to three heteroatoms selected independently from N, O and S and which is unsubstituted or substituted with one to three $R^4$, five- to ten-membered heteroaryl comprising one to four heteroatoms selected independently from N, O and S and which is unsubstituted or substituted with one to three $R^4$, 2-methylphenyl, 2-methoxyphenyl, 2-chlorophenyl, 2-methoxymethylphenyl, 2-(dimethylamino)methylphenyl, 2-(dimethylamino)methyl-6-methylphenyl, 2-methoxymethyl-6-methylphenyl, 4-cyano-2,6-dimethylphenyl, 2-methoxy-6-methylphenyl, 2-fluoro-6-methylphenyl, 2-chloro-6-methylphenyl, 4-chloro-2,6-dimethylphenyl, 2,6-dimethyl-4-methoxyphenyl, 2,6-dimethyl-4-fluorophenyl and 2,6-dimethyl-3-fluorophenyl; when $R^1$ is —C(O)C$_1$-C$_6$alkyl, —C(O)OC$_1$-C$_6$alkyl or —C$_1$-C$_6$alkylOC(O)OC$_1$-C$_6$alkyl then $R^2$ is selected from the group consisting of C$_1$-C$_6$alkyl unsubstituted or substituted with one to three $R^3$, C$_3$-C$_7$cycloalkyl unsubstituted or substituted with one to three $R^4$, C$_6$-C$_{12}$bicycloalkyl unsubstituted or substituted with one to three $R^4$, four- to seven-membered heterocycloalkyl comprising one to three heteroatoms selected independently from N, O and S and which is unsubstituted or substituted with one to three $R^4$, C$_6$-C$_{10}$aryl unsubstituted or substituted with one to three $R^4$, five- to ten-membered heteroaryl comprising one to four heteroatoms selected independently from N, O and S and which is unsubstituted or substituted with one to three $R^4$, $R^3$ at each occurrence is independently selected from the group consisting of halo, cyano, hydroxy, di(C$_1$-C$_3$alkyl)amino, (C$_1$-C$_3$alkyl)amino and amino; and $R^4$ at each occurrence is independently selected from halo, hydroxy, cyano, C$_1$-C$_3$alkyl, C$_1$-C$_3$alkoxy, C$_1$-C$_3$alkoxyC$_1$-C$_3$alkyl, di(C$_1$-C$_3$alkyl)amino, (C$_1$-C$_3$alkyl)amino, amino, di(C$_1$-C$_3$alkyl)amino-C$_1$-C$_3$alkyl, (C$_1$-C$_3$alkyl)amino-C$_1$-C$_3$alkyl, amino-C$_1$-C$_3$alkyl and four- to seven-membered heterocycloalkyl comprising one to three heteroatoms selected independently from N, O and S; or a pharmaceutically acceptable salt thereof.

E2 is a compound of E1 wherein $R^1$ is hydrogen; or a pharmaceutically acceptable salt thereof.

E3 is the compound of E2 wherein $R^2$ is selected from the group consisting of ethyl, isopropyl, 2-methylpropyl, C$_1$-C$_6$alkyl substituted with one to three $R^3$, cyclopropyl substituted with one to three $R^4$, C$_4$-C$_7$cycloalkyl unsubstituted or substituted with one to three $R^4$, and C$_6$-C$_{12}$bicycloalkyl unsubstituted or substituted with one to three $R^4$; or a pharmaceutically acceptable salt thereof.

E4 is the compound of E3 selected from the group consisting of: (3S)-3-({N-[(4-methoxy-1H-indol-2-yl)carbonyl]-L-leucyl}amino)-2-oxo-4-[(3S)-2-oxopyrrolidin-3-yl]butyl N,N-dimethylglycinate; (3S)-3-({N-[(4-methoxy-1H-indol-2-yl)carbonyl]-L-leucyl}amino)-2-oxo-4-[(3S)-2-oxopyrrolidin-3-yl]butyl N,N-dimethyl-D-alaninate; (3S)-3-({N-[(4-methoxy-1H-indol-2-yl)carbonyl]-L-leucyl}amino)-2-oxo-4-[(3S)-2-oxopyrrolidin-3-yl]butyl N,N,2-trimethylalaninate; (3S)-3-({N-[(4-methoxy-1H-indol-2-yl)carbonyl]-L-leucyl}amino)-2-oxo-4-[(3S)-2-oxopyrrolidin-3-yl]butyl 4-(dimethylamino)-2,2-di methylbutanoate; (3S)-3-({N-[(4-methoxy-1H-indol-2-yl)carbonyl]-L-leucyl}amino)-2-oxo-4-[(3S)-2-oxopyrrolidin-3-yl]butyl 4-(dimethylamino)butanoate; (3S)-3-({N-[(4-methoxy-1H-indol-2-yl)carbonyl]-L-leucyl}amino)-2-oxo-4-[(3S)-2-oxopyrrolidin-3-yl]butyl propanoate; (3S)-3-({N-[(4-methoxy-1H-indol-2-yl)carbonyl]-L-leucyl}amino)-2-oxo-4-[(3S)-2-oxopyrrolidin-3-yl]butyl 2-methylpropanoate; (3S)-3-({N-[(4-methoxy-1H-indol-2-yl)carbonyl]-L-leucyl}amino)-2-oxo-4-[(3S)-2-oxopyrrolidin-3-yl]butyl cyclohexanecarboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclohexanecarboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclobutanecarboxylate; (3S)-3-({N-[(4-methoxy-1H-indol-2-yl)carbonyl]-L-leucyl}amino)-2-oxo-4-[(3S)-2-oxopyrrolidin-3-yl]butyl (2S)-2-methylbutanoate; (3S)-3-({N-[(4-methoxy-1H-indol-2-yl)carbonyl]-L-leucyl}amino)-2-oxo-4-[(3S)-2-oxopyrrolidin-3-yl]butyl (2R)-2-methylbutanoate; (3S)-3-({N-[(4-methoxy-1H-indol-2-yl)carbonyl]-L-leucyl}amino)-2-oxo-4-[(3S)-2-oxopyrrolidin-3-yl]butyl bicyclo[1.1.1]pentane-1-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclopropanecarboxylate; and (3S)-3-({N-[(4-methoxy-1H-indol-2-yl)carbonyl]-L-leucyl}amino)-2-oxo-4-[(3S)-2-oxopyrrolidin-3-yl]butyl L-valinate; or a pharmaceutically acceptable salt thereof.

E5 is a compound of E1 or E2 wherein $R^2$ is a four- to seven-membered heterocycloalkyl comprising one to three heteroatoms selected independently from N, O and S and which is unsubstituted or substituted with one to three $R^4$; or a pharmaceutically acceptable salt thereof.

E6 is a compound of E5 wherein $R^2$ is selected from the group consisting of azetidinyl, pyrrolidinyl, piperidinyl and morpholinyl; each of which is unsubstituted or substituted with one to two $R^4$; or a pharmaceutically acceptable salt thereof.

E7 is a compound of the E6 wherein $R^2$ is selected from the group consisting of azetidinyl, pyrrolidinyl, piperidinyl and morpholinyl; each of which is substituted with one to two methyl; or a pharmaceutically acceptable salt thereof.

E8 is a compound of E7 which is selected from the group consisting of: (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethylpiperidine-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,3-di methylazetidine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl (3R)-1-methylpyrrolidine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl (3S)-1-methylpyrrolidine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-D-prolinate; (3S)-3-({N-[(4-methoxy-1H-indol-2-yl)carbonyl]-L-leucyl}amino) oxo-4-[(3S)-2-oxopyrrolidin-3-yl]butyl 1-methyl-L-prolinate; (3S)-3-({N-[(4-methoxy-1H-indol-2-yl)carbonyl]-L-leucyl}amino)-2-oxo-4-[(3S)-2-oxopyrrolidin-3-yl]butyl 1-methylpiperidine-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl (2R)-4-methylmorpholine-2-carboxylate; (3S)-3-({N-[(4-methoxy-1H-indol-2-yl)carbonyl]-L-leucyl}amino)-2-oxo-4-[(3S)-2-oxopyrrolidin-3-yl]butyl (2S)-1-methylpiperidine-2-carboxylate; (3S)-3-({N-[(4-methoxy-1H-indol-2-yl)carbonyl]-L-leucyl}amino)-2-oxo-4-[(3S)-2-oxopyrrolidin-3-yl]butyl (2S)-4-methylmorpholine-2-carboxylate; and (3S)-3-({N-[(4-methoxy-1H-indol-2-yl)carbonyl]-L-leucyl}amino)-2-oxo-4-[(3S)-2-oxopyrrolidin-3-yl]butyl (2R)-1-methylpiperidine-2-carboxylate; or a pharmaceutically acceptable salt thereof.

E9 is a compound of E1 or E2 wherein $R^2$ is a five- to ten-membered heteroaryl comprising one to four heteroatoms selected independently from N, O and S and which is unsubstituted or substituted with one to three $R^4$; or a pharmaceutically acceptable salt thereof.

E10 is a compound of the E9 wherein $R^2$ is an imidazolyl, pyrazolyl, isoxazolyl, pyridinyl or pyrimidinyl, each of which is unsubstituted or substituted with one to three $R^4$; or a pharmaceutically acceptable salt thereof.

E11 is a compound of E10 wherein $R^4$ at each occurrence is independently selected from methyl, methoxy, ethoxy, methoxymethyl, methylamino, (dimethylamino)methyl and tetrahydropyranyl; or a pharmaceutically acceptable salt thereof.

E12 is a compound of E11 selected from the group consisting of: (3S)-3-({N-[(4-methoxy-1H-indol-2-yl)carbonyl]-L-leucyl}amino)-2-oxo-4-[(3S)-2-oxopyrrolidin-3-yl]butyl 4-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl pyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl pyridine-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl pyridine-2-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,3-dimethyl-1H-pyrazole-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,5-dimethyl-1H-imidazole-4-carboxylate; (3S)-3-({N-[(4-methoxy-1H-indol-2-yl)carbonyl]-L-leucyl}amino)-2-oxo-4-[(3S) oxopyrrolidin-3-yl]butyl 1-methyl-1H-pyrazole-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-pyrazole-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-pyrazole-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-2-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4-methoxy-1-methyl-1H-imidazole-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,3,5-trimethyl-1H-pyrazole-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethyl-1H-pyrazole-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethyl-1H-pyrazole-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)-4-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4-(methoxymethyl)-6-methylpyrimidine-5-carboxylate; (3S)-3-({N-[(4-methoxy-1H-indol-2-yl)carbonyl]-L-leucyl}amino)-2-oxo-4-[(3S)-2- oxopyrrolidin-3-yl]butyl 4-(methoxymethyl)-2-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]-4-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4-[(dimethylamino)methyl]-6-methylpyrimidine-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4-[(dimethylamino)methyl]-2-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2,4-dimethylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4-methyl-2-(methylamino)pyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2-ethoxy-4-methylpyridine-3-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 3,5-dimethylpyridine-4-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2,4,6-trimethylpyrimidine carboxylate; (3S)-3-({N-[(4-methoxy-1H-indol-2-yl)carbonyl]-L-leucyl}amino)-2-oxo-4-[(3S)-2-oxopyrrolidin-3-yl]butyl 4,6-di methylpyrimidine-5-carboxylate; (3S)-3-({N-[(4-methoxy-1H-indol-2-yl)carbonyl]-L-leucyl}amino)-2-oxo-4-[(3S)-2-oxopyrrolidin-3-yl]butyl 2-fluoro-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 4,6-dimethyl-2-(tetrahydro-2H-pyran-4-yl)pyrimidine-5-carboxylate; and (3S)-3-({N-[(4-methoxy-1H-indol-2-yl)carbonyl]-L-leucyl}amino)-2-oxo-4-[(3S)-2-oxopyrrolidin-3-yl]butyl 3,5-dimethyl-1,2-oxazole-4-carboxylate; or a pharmaceutically acceptable salt thereof.

E13 is the compound of E2 selected from the group consisting of: (3S)-3-({N-[(4-methoxy-1H-indol-2-yl)carbonyl]-L-leucyl}amino)-2-oxo-4-[(3S)-2-oxopyrrolidin-3-yl]butyl 2-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-methoxybenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-chlorobenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)benzoate; (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]benzoate; (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 4-cyano-2,6-dimethyl benzoate; (3S)-3-({N-[(4-methoxy-1H-indol-2-yl)carbonyl]-L-leucyl}amino)-2-oxo-4-[(3S)-2-oxopyrrolidin-3-yl]butyl 2-methoxy-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-chloro-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 4-chloro-2,6-dimethylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 2-fluoro-6-methylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 4-methoxy-2,6-dimethylbenzoate; (3S)-3-({N-[(4-methoxy-1H-indol-2-yl)carbonyl]-L-leucyl}amino)-2-oxo-4-[(3S)-2-oxopyrrolidin-3-yl]butyl 4-fluoro-2,6-dimethylbenzoate; and (3S)-3-({N-[(4-methoxy-1H-indol-2-yl)carbonyl]-L-leucyl}amino)-2-oxo-4-[(3S) oxopyrrolidin-3-yl]butyl 3-fluoro-2,6-dimethylbenzoate; or a pharmaceutically acceptable salt thereof.

E14 is the compound of E1 wherein $R^1$ is —C(O)$C_1$-$C_6$alkyl, —C(O)O$C_1$-$C_6$alkyl and —$C_1$-$C_6$alkylOC(O)O$C_1$-$C_6$alkyl; or a pharmaceutically acceptable salt thereof.

E15 is a compound of E14 wherein $R^1$ is —C(O)$CH_3$, —C(O)O$CH_3$ or —CH($CH_3$)OC(O)O$CH_3$; or a pharmaceutically acceptable salt thereof.

E16 is a compound of E14 or E15 wherein $R^2$ is a $C_6$-$C_{10}$aryl which is unsubstituted or substituted with one to three $R^4$; or a pharmaceutically acceptable salt thereof.

E17 is a compound of E16 wherein $R^2$ is phenyl which is unsubstituted or substituted with one to three $R^4$; or a pharmaceutically acceptable salt thereof.

E18 is a compound of E17 wherein $R^2$ is 2,6-dimethylphenyl; or a pharmaceutically acceptable salt thereof.

E19 is the compound of E18 selected from the group consisting of: (3S)-4-[(3S)-1-acetyl-2-oxopyrrolidin-3-yl]-3-({N-[(4-methoxy-1H-indol-2-yl)carbonyl]-L-leucyl}amino)-2-oxobutyl 2,6-dimethylbenzoate; (3S)-3-[(2S)-4-[(2,6-dimethylbenzoyl)oxy]-2-({N-[(4-methoxy-1H-indol-2-yl)carbonyl]-L-leucyl}amino)-3-oxobutyl]-2-oxopyrrolidine-1-carboxylate; and (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl 2,6-dimethylbenzoate; or a pharmaceutically acceptable salt thereof.

E20 is a pharmaceutical composition comprising a therapeutically effective amount of a compound of any one of E1 to E19 or a pharmaceutically acceptable salt thereof together with a pharmaceutically acceptable carrier.

E21 is the pharmaceutical composition of E20 further comprising one or more additional therapeutic agents.

E22 is the pharmaceutical composition of E21 wherein the additional therapeutic agent is selected from azithromycin and remdesivir.

E23 is the pharmaceutical composition of E21 wherein the one or more additional therapeutic agent is selected from the group consisting of remdesivir, galidesivir, favilavir/avifavir, mulnupiravir (MK-4482/EIDD 2801), AT-527, AT-301, BLD-2660, favipiravir, camostat, SLV213 emtricitabine/tenofivir, clevudine, dalcetrapib, boceprevir, ABX464, dexamethasone, hydrocortisone, convalescent plasma, gelsolin (Rhu-p65N), monoclonal antibodies, regdanvimab (Regkirova), ravulizumab (Ultomiris), VIR-7831/VIR-7832, BRII-196/BRII-198, COVI-AMG/COVIDROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, PB1046, dapaglifozin, abivertinib, ATR-002, bemcentinib, acalabrutinib, baricitinib, losmapimod, famotidine, niclosamide and diminazene.

E24 is the pharmaceutical composition of E23 wherein the one or more additional therapeutic agent is selected from the group consisting of remdesivir, dexamethasone, malnupiravir, bamlanivimab and baricitinib.

E25 is the pharmaceutical composition of any one of E20 to E24 wherein the pharmaceutical composition is in the form of an oral dosage form.

E26 is the pharmaceutical composition of E25 wherein the pharmaceutical composition is in the form of a tablet or capsule.

E27 is the pharmaceutical composition of any one of E20 to E24 wherein the pharmaceutical composition is in the form of an intranasal dosage form.

E28 is a method of treating COVID-19 in a patient, the method comprising administering a therapeutically effective amount of a compound of any one of E1 to E19 or a pharmaceutically acceptable salt thereof to a patient in need thereof.

E29 is the method of E28 E21 further comprising administering one or more additional therapeutic agents to the patient in need thereof.

E30 is the method of E29 wherein the one or more additional therapeutic agent is selected from the group consisting of remdesivir, galidesivir, favilavir/avifavir, mulnupiravir (MK-4482/EIDD 2801), AT-527, AT-301, BLD-2660, favipiravir, camostat, SLV213 emtrictabine/tenofivir, clevudine, dalcetrapib, boceprevir, ABX464, dexamethasone, hydrocortisone, convalescent plasma, gelsolin (Rhu-p65N), monoclonal antibodies, regdanvimab (Regkirova), ravulizumab (Ultomiris), VIR-7831/VIR-7832, BRII-196/BRII-198, COVI-AMG/COVIDROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab, otilimab, casirivimab/imdevimab (REGN-Cov2), MK-7110 (CD24Fc/SACCOVID), heparin, apixaban, tocilizumab (Actemra), sarilumab (Kevzara), apilimod dimesylate, DNL758, PB1046, dapaglifozin, abivertinib, ATR-002, bemcentinib, acalabrutinib, baricitinib, losmapimod, famotidine, niclosamide and diminazene.

E31 is the method of E30 wherein the one or more additional therapeutic agent is selected from the group consisting of remdesivir, dexamethasone, malnupiravir, bamlanivimab and baricitinib.

E32 is a method of treating COVID-19 in a patient, the method comprising administering a pharmaceutical composition of any one of E20 to E27 to a patient in need thereof.

E33 is a method of inhibiting or preventing SARS-CoV-2 viral replication comprising contacting the SARS-CoV-2 coronavirus 3CL protease with a therapeutically effective amount of a compound of any one of E1 to E19 or a pharmaceutically acceptable salt thereof.

E34 is a method of inhibiting or preventing SARS-CoV-2 viral replication in a patient the method comprising administering to the patient in need of inhibition of or prevention of SARS-CoV-2 viral replication a therapeutically effective amount of a compound of any one of E1 to E19 or a pharmaceutically acceptable salt thereof.

It is to be understood that the method of treatment embodiments of the invention can also to be construed as medical use-type embodiments (such as E35 and E36 below) or alternatively second medical use-type embodiments (such as E37 below).

E35 is a compound according to any one of E1 to E19 or a pharmaceutically acceptable salt thereof for use in the treatment of COVID-19.

E36 is a pharmaceutical composition according to any one of E20 to E27 for use in the treatment of COVID-19.

E37 is a compound according to any one of E1 to E19 or a pharmaceutically acceptable salt thereof for use in the preparation of a medicament for the treatment of COVID-19.

The present invention also provides a method of treating a condition that is mediated by SARS-CoV-2 coronavirus 3C-like protease activity in a patient by administering to said patient a pharmaceutically effective amount of a SARS-CoV-2 protease inhibitor as described herein.

The present invention also provides a method of targeting SARS-CoV-2 inhibition as a means of treating indications caused by SARS-CoV-2-related viral infections.

The present invention also provides a method of identifying cellular or viral pathways interfering with the functioning of the members of which could be used for treating indications caused by SARS-CoV-2 infections by administering a SARS-CoV-2 protease inhibitor as described herein.

The present invention also provides a method of using SARS-CoV-2 protease inhibitors as described herein as tools for understanding mechanism of action of other SARS-CoV-2 inhibitors.

The present invention also provides a method of using SARS-CoV-2 3C-like protease inhibitors for carrying out gene profiling experiments for monitoring the up or down regulation of genes for the purposed of identifying inhibitors for treating indications caused by SARS-CoV-2 infections such as COVID-19.

The present invention further provides a pharmaceutical composition for the treatment of COVID-19 in a mammal containing an amount of a SARS-CoV-2 3C-like protease inhibitor that is effective in treating COVID-19 and a pharmaceutically acceptable carrier.

DETAILED DESCRIPTION OF THE INVENTION

Figure 1:
FIG. 1 depicts the residue differences between SARS-CoV and SARS-CoV-2, with an inhibitor compound shown at the active site.

For the purposes of the present invention, as described and claimed herein, the following terms are defined as follows:

As used herein, the terms "comprising" and "including" are used in their open, non-limiting sense. The term "treating", as used herein, unless otherwise indicated, means reversing, alleviating, inhibiting the progress of, or preventing the disorder of condition to which such term applies, or one or more symptoms of such disorder or condition. In the methods of treating COVID-19 it is to be understood that COVID-19 is the disease caused in patients by infection with the SARS-CoV-2 virus. The SARS-CoV-2 virus is to be understood to encompass the initially discovered strain of the virus as well as mutant strains which emerge, such as but not limited to, strains such as B.1.1.7 (UK variant), B.1.351 (South African variant) and P.1 (Brazilian variant). The term "treatment", as used herein, unless otherwise indicated, refers to the act of treating as "treating" is defined immediately above.

The term "alkyl" as used herein refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. An alkoxy group which is attached to an alkyl group is referred to as an alkoxyalkyl. An example of an alkoxyalkyl group is methoxymethyl.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$alkyl" or "$C_{1-6}$ alkyl" refers to an alkyl substituent containing from 1 to 6 carbon atoms and "$C_1$-$C_3$alkyl" refers to an alkyl substituent containing from 1 to 3 carbon atoms. The term "$C_1$-$C_3$alkoxy" refers to an alkoxy group containing from 1 to 3 carbon atoms, such as methoxy, ethoxy, propoxy and isopropoxy. Illustrating further, $C_3$-$C_6$cycloalkyl or $C_{3-6}$-cycloalkyl refers to saturated cycloalkyl group containing from 3 to 6 carbon ring atoms as described further below.

The term "cycloalkyl" refers to a carbocyclic substituent obtained by removing a hydrogen from a saturated carbocyclic molecule, for example one having three to seven carbon atoms. The term "cycloalkyl" includes monocyclic saturated carbocycles. The term "$C_3$-$C_7$cycloalkyl" means a radical of a three- to seven-membered ring system which includes the groups cyclopropyl, cyclobutyl, cyclopentyl, cyclohexyl, and cycloheptyl and the term "$C_4$-$C_7$cycloalkyl" means a four- to seven-membered ring system. The term "$C_{3-6}$cycloalkyl" means a radical of a three- to six-membered ring system which includes the groups cyclopropyl, cyclobutyl, cyclopentyl and cyclohexyl. The term "$C_{3-6}$cycloalkoxy" refers to a three- to six-membered cycloalkyl group attached to an oxygen radical. Examples include cyclopropoxy, cyclobutoxy, cyclopentoxy and cyclohexoxy. The term "$C_5$-$C_{12}$bicycloalkyl" means bicyclic cycloalkyl moieties such as bicyclopentyl, bicyclohexyl, bicycloheptyl, bicyclooctyl, bicyclononyl, spiropentyl, spirohexyl, spiroheptyl, spirooctyl and spirononyl.

The term "aryl" refers to a radical of a carbocyclic aromatic ring system. The term "$C_6$-$C_{10}$ aryl" means an aryl with 6 to 10 carbon atoms, such as a phenyl or naphthyl group.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms and "4- to 7-membered heterocycloalkyl" refers to a heterocycloalkyl containing from 4 to 7 atoms, each including one to three heteroatoms, in the cyclic moiety of the heterocycloalkyl. Likewise, the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore, the phases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol. The term cyano refers to a —CN group.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring.

In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, and pyrazolo[1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydro-quinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (———), a solid wedge ( ▬ ), , or a dotted wedge ( ⁃⁃⁃⁃⁃⁃ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. The compounds of Formula I may exhibit the phenomenon of tautomerism; such tautomers are also regarded as compounds of the invention. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof.

The phrase "pharmaceutically acceptable salts(s)", as used herein, unless otherwise indicated, includes salts of acidic or basic groups which may be present in the compounds described herein. The compounds used in the methods of the invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isethionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

With respect to the compounds of the invention used in the methods of the invention, if the compounds also exist as tautomeric forms then this invention relates to those tautomers and the use of all such tautomers and mixtures thereof.

The subject invention also includes compounds and methods of treatment of COVID-19 and methods of inhibiting SARS-CoV-2 with isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or isotopes of other atoms are with the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds used in the methods of this invention and prodrugs thereof can generally be prepared by carrying out the procedures for preparing the compounds disclosed in the art by substituting a readily available isotopically labelled reagent for a non-isotopically labelled reagent.

This invention also encompasses methods using pharmaceutical compositions and methods of treating COVID-19 infections through administering prodrugs of compounds of the invention. Compounds having free amido or hydroxy groups can be converted into prodrugs. Prodrugs include compounds wherein an amino acid residue, or a polypeptide chain of two or more (e.g., two, three or four)amino acid residues is covalently joined through an ester bond to a hydroxy of compounds used in the methods of this invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 1996, 29, 10. Free amines can also be derivatized as amides, sulfonamides or phosphonamides. All of these prodrug moieties may incorporate groups including but not limited to ether, amine and carboxylic acid functionalities.

The compounds of the present invention can be used in the methods of the invention in combination with other drugs. For example, dosing a SARS-CoV-2 coronavirus infected patient (i.e. a patient with COVID-19) with the SARS-CoV-2 coronavirus 3CL protease inhibitor of the invention and an interferon, such as interferon alpha, or a pegylated interferon, such as PEG-Intron or Pegasus, may provide a greater clinical benefit than dosing either the interferon, pegylated interferon or the SARS-CoV-2 coronavirus inhibitor alone. Other additional agents that can be used in the methods of the present invention include azithromycin and remdesivir. Examples of greater clinical benefits could include a larger reduction in COVID-19 symptoms, a faster time to alleviation of symptoms, reduced lung pathology, a larger reduction in the amount of SARS-Cov-2 coronavirus in the patient (viral load), and decreased mortality.

The SARS-Cov-2 coronavirus infects cells which express p-glycoprotein. Some of the SARS-Cov-2 coronavirus 3CL protease inhibitors of the invention are p-glycoprotein substrates. Compounds which inhibit the SARS-Cov-2 coronavirus which are also p-glycoprotein substrates may be dosed with p-glycoprotein inhibitor. Examples of p-glycoprotein inhibitors are verapamil, vinblastine, ketoconazole, nelfinavir, ritonavir or cyclosporine. The p-glycoprotein inhibitors act by inhibiting the efflux of the SARS-Cov-2 coronavirus inhibitors of the invention out of the cell. The inhibition of the p-glycoprotein based efflux will prevent reduction of intracellular concentrations of the SARS-Cov-2 coronavirus inhibitor due to p-glycoprotein efflux. Inhibition of the p-glycoprotein efflux will result in larger intracellular concentrations of the SARS-CoV-2 coronavirus inhibitors. Dosing a SARS-CoV-2 coronavirus infected patient with the SARS-CoV-2 coronavirus 3CL protease inhibitors of the invention and a p-glycoprotein inhibitor may lower the amount of SARS-Cov-2 coronavirus 3CL protease inhibitor required to achieve an efficacious dose by increasing the intracellular concentration of the SARS-CoV-2 coronavirus 3CL protease inhibitor.

Among the agents that may be used to increase the exposure of a mammal to a compound of the present invention are those that can as inhibitors of at least one isoform of the cytochrome P450 (CYP450) enzymes. The isoforms of CYP450 that may be beneficially inhibited included, but are not limited to CYP1A2, CYP2D6, CYP2C9, CYP2C19 and CYP3A4. The compounds used in the methods of the invention include compounds that may be CYP3A4 substrates and are metabolized by CYP3A4. Dosing a SARS-CoV-2 coronavirus infected patient with a SARS-CoV-2 coronavirus inhibitor which is a CYP3A4 substrate, such as SARS-CoV-2 coronavirus 3CL protease inhibitor, and a CYP3A4 inhibitor, such as ritonavir, nelfinavir or delavirdine, will reduce the metabolism of the SARS-Cov-2 coronavirus inhibitor by CYP3A4. This will result in reduced clearance of the SARS-CoV-2 coronavirus inhibitor and increased SARS-Cov-2 coronavirus inhibitor plasma concentrations. The reduced clearance and higher plasma concentrations may result in a lower efficacious dose of the SARS-CoV-2 coronavirus inhibitor.

Additional therapeutic agents that can be used in combination with the SARS-CoV-2 inhibitors in the methods of the present invention include the following:

PLpro inhibitors: Ribavirin, Valganciclovir, β-Thymidine, Aspartame, Oxprenolol, Doxycycline, Acetophenazine, Iopromide, Riboflavin, Reproterol, 2,2'-Cyclocytidine, Chloramphenicol, Chlorphenesin carbamate, Levodropropizine, Cefamandole, Floxuridine, Tigecycline, Pemetrexed, L(+)-Ascorbic acid, Glutathione, Hesperetin, Ademetionine, Masoprocol, Isotretinoin, Dantrolene, Sulfasalazine Anti-bacterial, Silybin, Nicardipine, Sildenafil, Platycodin, Chrysin, Neohesperidin, Baicalin, Sugetriol-3,9-diacetate, (−)-Epigallocatechin gallate, Phaitanthrin D, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, 2,2-Di(3-indolyl)-3-indolone, (S)-(1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl-2-amino-3-phenylpropanoate, Piceatannol, Rosmarinic acid, and Magnolol.

3CLpro inhibitors: Lymecycline, Chlorhexidine, Alfuzosin, Cilastatin, Famotidine, Almitrine, Progabide, Nepafenac, Carvedilol, Amprenavir, Tigecycline, Montelukast, Carminic acid, Mimosine, Flavin, Lutein, Cefpiramide, Phenethicillin, Candoxatril, Nicardipine, Estradiol valerate, Pioglitazone, Conivaptan, Telmisartan, Doxycycline, Oxytetracycline, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl5-((R)-1,2-dithiolan-3-yl) pentanoate, Betulonal, Chrysin-7-O-β-glucuronide, Andrographiside, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 2-nitrobenzoate, 2β-Hydroxy-3,4-seco-friedelolactone-27-oic acid (S)-(1S, 2R,4aS,5R,8aS)-1-Formamido-1,4a-dimethyl-6-methylene-5-((E)-2-(2-oxo-2,5-dihydrofuran-3-yl)ethenyl) decahydronaphthalen-2-yl-2-amino-3-phenylpropanoate, Isodecortinol, Cerevisterol, Hesperidin, Neohesperidin, Andrograpanin, 2-((1R,5R,6R,8aS)-6-Hydroxy-5-(hydroxymethyl)-5,8a-dimethyl-2-methylenedecahydronaphthalen-1-yl)ethyl benzoate, Cosmosiin, Cleistocaltone A, 2,2-Di(3-indolyl)-3-indolone, Biorobin, Gnidicin, Phyllaemblinol, Theaflavin 3,3'-di-O-gallate, Rosmarinic acid, Kouitchenside 1, Oleanolic acid, Stigmast-5-en-3-ol, Deacetylcentapicrin, and Berchemol.

RdRp inhibitors: Valganciclovir, Chlorhexidine, Ceftibuten, Fenoterol, Fludarabine, Itraconazole, Cefuroxime, Atovaquone, Chenodeoxycholic acid, Cromolyn, Pancuronium bromide, Cortisone, Tibolone, Novobiocin, Silybin, Idarubicin Bromocriptine, Diphenoxylate, Benzylpenicilloyl G, Dabigatran etexilate, Betulonal, Gnidicin, 2β,30β-Dihydroxy-3,4-seco-friedelolactone-27-lactone, 14-Deoxy-11,12-didehydroandrographolide, Gniditrin, Theaflavin 3,3'-di-O-gallate, (R)-((1R,5aS,6R,9aS)-1,5a-Dimethyl-7-methylene-3-oxo-6-((E)-2-(2-oxo-2,5-dihydrofuran-3-yl)ethenyl)decahydro-1H-benzo[c]azepin-1-yl)methyl2-amino-3-phenylpropanoate, 2β-Hydroxy-3,4-seco-friedelolactone-27-oic acid, 2-(3,4-Dihydroxyphenyl)-2-[[2-(3,4-dihydroxyphenyl)-3,4-dihydro-5,7-dihydroxy-2H-1-benzopyran-3-yl]oxy]-3,4-dihydro-2H-1-benzopyran-3,4,5,7-tetrol, Phyllaemblicin B, 14-hydroxycyperotundone, Andrographiside, 2-((1R,5R,6R,8aS)-6-Hydroxy-5-(hydroxymethyl)-5,8a-dimethyl-2-methylenedecahydro naphthalen-1-yl)ethyl benzoate, Andrographolide, Sugetriol-3,9-diacetate, Baicalin, (1S,2R,4aS,5R,8aS)-1-Formamido-1,4a-dimethyl-6-methylene-5-((E)-2-(2-oxo-2,5-dihydrofuran-3-yl)ethenyl)decahydronaphthalen-2-yl 5-((R)-1,2-dithiolan-3-yl)pentanoate, 1,7-Dihydroxy-3-methoxyxanthone, 1,2,6-Trimethoxy-8-[(6-O-β-D-xylopyranosyl-β-D-glucopyranosyl)oxy]-9H-xanthen-9-one, and 1,8-Dihydroxy-6-methoxy-2-[(6-O-β-D-xylopyranosyl-β-D-glucopyranosyl)oxy]-9H-xanthen-9-one, 8-(β-D-Glucopyranosyloxy)-1,3,5-trihydroxy-9H-xanthen-9-one.

Additional therapeutic agents that can be used in the methods of the invention include Diosmin, Hesperidin, MK-3207, Venetoclax, Dihydroergocristine, Bolazine, R428, Ditercalinium, Etoposide, Teniposide, UK-432097, Irinotecan, Lumacaftor, Velpatasvir, Eluxadoline, Ledipasvir, Lopinavir/Ritonavir+Ribavirin, Alferon, and prednisone. Other additional agents useful in the methods of the present invention include chloroquine, hydroxychloroquine, azithromycin and remdesivir.

Other additional agents that can be used in the methods of the present invention include α-ketoamides compounds designated as 11r, 13a and 13b, shown below, as described in Zhang, L.; Lin, D.; Sun, X.; Rox, K.; Hilgenfeld, R.; X-ray Structure of Main Protease of the Novel Coronavirus SARS-CoV-2 Enables Design of α-Ketoamide Inhibitors; bioRxiv preprint doi: https://doi.org/10.1101/2020.02.17.952879

-continued

13b

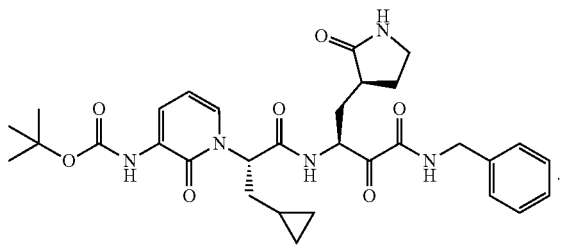

Additional agents that can be used in the methods and compositions of the present invention include RIG 1 pathway activators such as those described in U.S. Pat. No. 9,884,876.

Other additional agents that can be used in the methods, uses and pharmaceutical compositions of the invention are one or more such agent selected from antivirals such as remdesivir, galidesivir, favilavir/avifavir, mulnupiravir (MK-4482/EIDD 2801), AT-527, AT-301, BLD-2660, favipiravir, camostat, SLV213 emtrictabine/tenofivir, clevudine, dalcetrapib, boceprevir and ABX464, glucocorticoids such as dexamethasone and hydrocortisone, convalescent plasma, a recombinant human plasma such as gelsolin (Rhu-p65N), monoclonal antibodies such as regdanvimab (Regkirova), ravulizumab (Ultomiris), VIR-7831/VIR-7832, BRII-196/BRII-198, COVI-AMG/COVIDROPS (STI-2020), bamlanivimab (LY-CoV555), mavrilimab, leronlimab (PRO140), AZD7442, lenzilumab, infliximab, adalimumab, JS 016, STI-1499 (COVIGUARD), lanadelumab (Takhzyro), canakinumab (Ilaris), gimsilumab and otilimab, antibody cocktails such as casirivimab/imdevimab (REGN-Cov2), recombinant fusion protein such as MK-7110 (CD24Fc/SACCOVID), anticoagulants such as heparin and apixaban, IL-6 receptor agonists such as tocilizumab (Actemra) and sarilumab (Kevzara), PlKfyve inhibitors such as apilimod dimesylate, RIPK1 inhibitors such as DNL758, VIP receptor agonists such as PB1046, SGLT2 inhibitors such as dapaglifozin, TYK inhibitors such as abivertinib, kinase inhibitors such as ATR-002, bemcentinib, acalabrutinib, baricitinib and losmapimod, H2 blockers such as famotidine, anthelmintics such as niclosamide, furin inhibitors such as diminazene.

The term "SARS-Cov-2 inhibiting agent" means any SARS-CoV-2 related coronavirus 3C like protease inhibitor compound described herein or a pharmaceutically acceptable salt, hydrate, prodrug, active metabolite or solvate thereof or a compound which inhibits replication of SARS-CoV-2 in any manner.

The term "interfering with or preventing" SARS-CoV-2-related coronavirus ("SARS-CoV-2") viral replication in a cell means to reduce SARS-CoV-2 replication or production of SARS-CoV-2 components necessary for progeny virus in a cell as compared to a cell not being transiently or stably transduced with the ribozyme or a vector encoding the ribozyme. Simple and convenient assays to determine if SARS-CoV-2 viral replication has been reduced include an ELISA assay for the presence, absence, or reduced presence of anti-SARS-CoV-2 antibodies in the blood of the subject (Nasoff, et al., PNAS 88:5462-5466, 1991), RT-PCR (Yu, et al., in Viral Hepatitis and Liver Disease 574-577, Nishioka, Suzuki and Mishiro (Eds.); Springer-Verlag, Tokyo, 1994). Such methods are well known to those of ordinary skill in the art. Alternatively, total RNA from transduced and infected "control" cells can be isolated and subjected to analysis by dot blot or northern blot and probed with SARS-CoV-2 specific DNA to determine if SARS-CoV-2 replication is reduced. Alternatively, reduction of SARS-CoV-2 protein expression can also be used as an indicator of inhibition of SARS-CoV-2 replication. A greater than fifty percent reduction in SARS-CoV-2 replication as compared to control cells typically quantitates a prevention of SARS-CoV-2 replication.

If a SARS-CoV-2 inhibitor compound used in the method of the invention is a base, a desired salt may be prepared by any suitable method known to the art, including treatment of the free base with an inorganic acid (such as hydrochloric acid, hydrobromic acid, sulfuric acid, nitric acid, phosphoric acid, and the like), or with an organic acid (such as acetic acid, maleic acid, succinic acid, mandelic acid, fumaric acid, malonic acid, pyruvic acid, oxalic acid, glycolic acid, salicylic acid, pyranosidyl acid (such as glucuronic acid or galacturonic acid), alpha-hydroxy acid (such as citric acid or tartaric acid), amino acid (such as aspartic acid or glutamic acid), aromatic acid (such as benzoic acid or cinnamic acid), sulfonic acid (such as p-toluenesulfonic acid or ethanesulfonic acid), and the like.

If a SARS-CoV-2 inhibitor compound used in the method of the invention is an acid, a desired salt may be prepared by any suitable method known to the art, including treatment of the free acid with an inorganic or organic base (such as an amine (primary, secondary, or tertiary)), an alkali metal hydroxide, or alkaline earth metal hydroxide. Illustrative examples of suitable salts include organic salts derived from amino acids (such as glycine and arginine), ammonia, primary amines, secondary amines, tertiary amines, and cyclic amines (such as piperidine, morpholine, and piperazine), as well as inorganic salts derived from sodium, calcium, potassium, magnesium, manganese, iron, copper, zinc, aluminum and lithium.

In the case of SARS-CoV-2 inhibitor compounds, prodrugs, salts, or solvates that are solids, it is understood by those skilled in the art that the hydroxamate compound, prodrugs, salts, and solvates used in the method of the invention, may exist in different polymorph or crystal forms, all of which are intended to be within the scope of the present invention and specified formulas. In addition, the hydroxamate compound, salts, prodrugs and solvates used in the method of the invention may exist as tautomers, all of which are intended to be within the broad scope of the present invention.

Solubilizing agents may also be used with the compounds of the invention to increase the compounds solubility in water of physiologically acceptable solutions. These solubilizing agents include cyclodextrans, propylene glycol, diethylacetamide, polyethylene glycol, Tween, ethanol and micelle forming agents. Offered solubilizing agents are cyclodextrans, particularly beta cyclodextrans and in particular hydroxypropyl betacyclodextran and sulfobutylether betacyclodextran.

In some cases, the SARS-CoV-2 inhibitor compounds, salts, prodrugs and solvates used in the method of the invention may have chiral centers. When chiral centers are present, the hydroxamate compound, salts, prodrugs and solvates may exist as single stereoisomers, racemates, and/or mixtures of enantiomers and/or diastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprised at least 90% of a single isomer (80% enantiomeric excess), more preferably at least 95% (90% e.e.), even more preferably at least 97.5% (95%) e.e.), and most preferably at least 99% (98% e.e.).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. In a preferred embodiment of the present invention, "treating" or "treatment" means at least the mitigation of a disease condition in a human, that is alleviated by the inhibition of the activity of the SARS-CoV-2 3C-like protease which is the main protease of SARS-CoV-2, the causative agent for COVID-19. For patients suffering from COVID-19 fever, fatigue, and dry cough are the main manifestations of the disease, while nasal congestion, runny nose, and other symptoms of the upper respiratory tract are rare. Beijing Centers for Diseases Control and Prevention indicated that the typical case of COVID-19 has a progressive aggravation process. COVID-19 can be classified into light, normal, severe, and critical types based on the severity of the disease National Health Commission of the People's Republic of China. Diagnosis and Treatment of Pneumonia Caused by 2019-nCoV (Trial Version 4). Available online: http://www.nhc.gov.cn/jkj/s3577/202002/573340613ab243b3a7f61df260551dd4/files/c7 91e5a7ea5149f680fdcb34dac0f54e.pdf (accessed on 6 Feb. 2020): (1) Mild cases—the clinical symptoms were mild, and no pneumonia was found on the chest computed tomography (CT); (2) normal cases—fever, respiratory symptoms, and patients found to have imaging manifestations of pneumonia; (3) severe cases—one of the following three conditions: Respiratory distress, respiratory rate 30 times/min (in resting state, refers to oxygen saturation 93%), partial arterial oxygen pressure (PaO2)/oxygen absorption concentration (FiO2) ≤300 mmHg (1 mmHg=0.133 kPa); (4) critical cases—one of the following three conditions: Respiratory failure and the need for mechanical ventilation, shock, or the associated failure of other organs requiring the intensive care unit. The current clinical data shows that the majority of the deaths occurred in the older patients. However, severe cases have been documented in young adults who have unique factors, particularly those with chronic diseases, such as diabetes or hepatitis B. Those with a long-term use of hormones or immunosuppressants, and decreased immune function, are likely to get severely infected.

Methods of treatment for mitigation of a disease condition such as COVID-19 include the use of one or more of the compounds in the invention in any conventionally acceptable manner. According to certain preferred embodiments of the invention, the compound or compounds used in the methods of the present invention are administered to a mammal, such as a human, in need thereof. Preferably, the mammal in need thereof is infected with a coronavirus such as the causative agent of COVID-19, namely SARS-CoV-2.

The present invention also includes prophylactic methods, comprising administering an effective amount of a SARS-CoV-2 inhibitor of the invention, or a pharmaceutically acceptable salt, prodrug, pharmaceutically active metabolite, or solvate thereof to a mammal, such as a human at risk for infection by SARS-CoV-2. According to certain preferred embodiments, an effective amount of one or more compounds of the invention, or a pharmaceutically acceptable salt, prodrug, pharmaceutically active metabolite, or solvate thereof is administered to a human at risk for infection by SARS-CoV-2, the causative agent for COVID-19. The prophylactic methods of the invention include the use of one or more of the compounds in the invention in any conventionally acceptable manner.

The following are examples of specific embodiments of the invention:

Certain of the compounds used in the methods of the invention are known and can be made by methods known in the art.

Recent evidence indicates that a new coronavirus SARS-Cov-2 is the causative agent of COVID-19. The nucleotide sequence of the SARS-CoV-2 coronavirus as well as the recently determined L- and S-subtypes have recently been determined and made publicly available.

The activity of the inhibitor compounds as inhibitors of SARS-CoV-2 viral activity may be measured by any of the suitable methods available in the art, including in vivo and in vitro assays. The activity of the compounds of the present invention as inhibitors of coronavirus 3C-like protease activity (such as the 3C-like protease of the SARS-CoV-2 coronavirus) may be measured by any of the suitable methods known to those skilled in the art, including in vivo and in vitro assays. Examples of suitable assays for activity measurements include the antiviral cell culture assays described herein as well as the antiprotease assays described herein, such as the assays described in the Example section.

Administration of the SARS-CoV-2 inhibitor compounds and their pharmaceutically acceptable prodrugs, salts, active metabolites, and solvates may be performed according to any of the accepted modes of administration available to those skilled in the art. Illustrative examples of suitable modes of administration include oral, nasal, pulmonary, parenteral, topical, intravenous, injected, transdermal, and rectal. Oral, intravenous, and nasal deliveries are preferred.

A SARS-CoV-2-inhibiting agent may be administered as a pharmaceutical composition in any suitable pharmaceutical form. Suitable pharmaceutical forms include solid, semi-solid, liquid, or lyophilized formulations, such as tablets, powders, capsules, suppositories, suspensions, liposomes, and aerosols. The SARS-CoV inhibiting agent may be prepared as a solution using any of a variety of methodologies. For example, SARS-CoV-2-inhibiting agent can be dissolved with acid (e.g., 1 M HCl) and diluted with a sufficient volume of a solution of 5% dextrose in water (D5W) to yield the desired final concentration of SARS-Cov-2-inhibiting agent (e.g., about 15 mM). Alternatively, a solution of D5W containing about 15 mM HCl can be used to provide a solution of the SARS-CoV-2-inhibiting agent at the appropriate concentration. Further, the SARS-Cov-2-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling and dissolving the ingredients as appropriate, to give the desired products for intravenous, oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of a SARS-CoV-2-inhibiting agent and preferably is made up of one or more pharmaceutical dosage units. The selected dose may be administered to a mammal, for example, a human patient, in need of treatment mediated by inhibition of SARS-Cov-2 related coronavirus activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion.

The phrases "therapeutically effective amount" and "effective amount" are intended to mean the amount of an inventive agent that, when administered to a mammal in need of treatment, is sufficient to effect treatment for injury or disease conditions alleviated by the inhibition of SARS-CoV-2 viral replication. The amount of a given SARS-CoV-2-inhibiting agent used in the method of the invention that will be therapeutically effective will vary depending upon factors such as the particular SARS-CoV-2-inhibiting agent, the disease condition and the severity thereof, the identity and characteristics of the mammal in need thereof, which amount may be routinely determined by those skilled in the art.

It will be appreciated that the actual dosages of the SARS-CoV-2-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.01 to about 1000 mg/kg body weight, preferably from about 0.1 to about 500 mg/kg body weight, and even more preferably from about 1 to about 500 mg/kg body weight, with courses of treatment repeated at appropriate intervals. For intravenous dosing a dose of up to 5 grams per day may be employed. Intravenous administration can occur for intermittent periods during a day or continuously over a 24-hour period.

The terms "cytochrome P450-inhibiting amount" and "cytochrome P450 enzyme activity-inhibiting amount", as used herein, refer to an amount of a compound required to decrease the activity of cytochrome P450 enzymes or a particular cytochrome P450 enzyme isoform in the presence of such compound. Whether a particular compound of decreases cytochrome P450 enzyme activity, and the amount of such a compound required to do so, can be determined by methods know to those of ordinary skill in the art and the methods described herein.

Protein functions required for coronavirus replication and transcription are encoded by the so-called "replicase" gene. Two overlapping polyproteins are translated from this gene and extensively processed by viral proteases. The C-proximal region is processed at eleven conserved interdomain junctions by the coronavirus main or "3C-like protease. The name "3C-like" protease derives from certain similarities between the coronavirus enzyme and the well-known picornavirus 3C proteases. These include substrate preferences, use of cysteine as an active site nucleophile in catalysis, and similarities in their putative overall polypeptide folds. A comparison of the amino acid sequence of the SARS-Cov-2-associated coronavirus 3C-like protease to that of other known coronaviruses such as SARS-CoV shows the amino acid sequences have approximately 96% shared homology.

Amino acids of the substrate in the protease cleavage site are numbered from the N to the C terminus as follows: -P3-P2-P1-P1'-P2'-P3', with cleavage occurring between the P1 and P1' residues (Schechter & Berger, 1967). Substrate specificity is largely determined by the P2, P1 and P1' positions. Coronavirus main protease cleavage site specificities are highly conserved with a requirement for glutamine at P1 and a small amino acid at P1' (Journal of General Virology, 83, pp. 595-599 (2002)).

The compounds used in the methods of the present invention can be prepared according to the methods set forth in Reaction Schemes 1 to 7 below.

Scheme 1

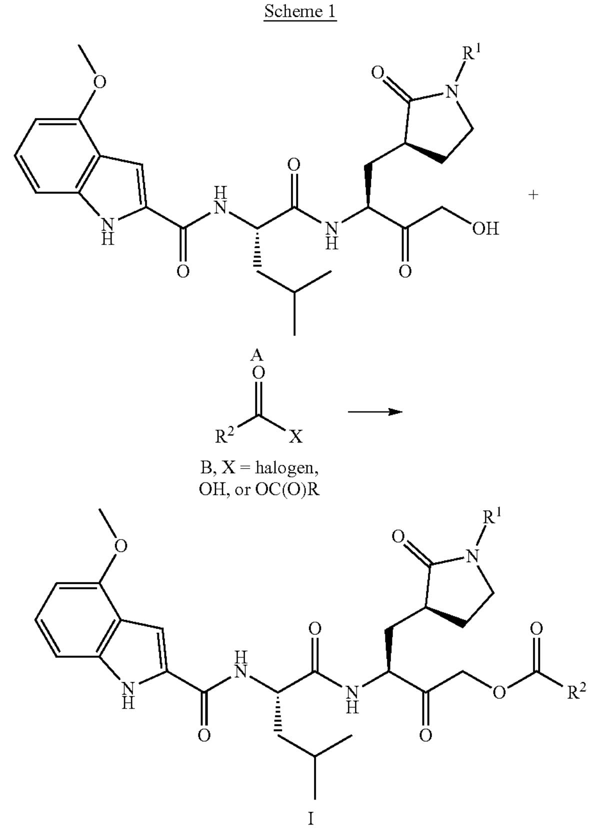

Scheme 1 illustrates a synthetic sequence for the preparation of compounds of Formula I as shown, wherein a compound of Formula A is treated with a compound of Formula B, wherein X is typically a halogen atom or OH. Such methods are well known to those skilled in the art. For example, when X is a halogen atom, the reaction between the acid halide R²C(O)X, B, and the hydroxy ketone, A, is conducted in the presence of a suitable base to consume the hydrogen halide HX produced as a by-product of the reaction. Examples of suitable bases include, but are not limited to, tertiary amines such as N-methyl morpholine (NMM), 2,6-dimethylpyridine, or diisopropylethylamine (DIEA), or inorganic bases such as magnesium oxide (MgO), sodium carbonate (Na₂CO₃), or potassium bicarbonate (KHCO₃). Suitable solvents include, but are not limited to, aprotic solvents such as dichloromethane (CH₂Cl₂), N,N-dimethylformamide (DMF), tetrahydrofuran (THF), or acetonitrile (CH₃CN). When X is OH, the compound B is a carboxylic acid of formula R²CO₂H and it is customary to use a reagent or combination of reagents to accelerate the reaction of the carboxylic acid B with the hydroxy ketone, A. One skilled in the art may choose to use, for example, a carbodiimide reagent such as 1-Ethyl-3-(3-dimethylaminopropyl)carbodiimide (EDC) or N,N'-dicyclohexyl carbodiimide (DCC), optionally in the presence of an auxiliary nucleophile such as hydroxybenzotriazole (HOBt) or 2-hydroxypyridine-N-oxide (HOPO). Further, when X is OH, one skilled in the art may choose to use reagents that are suitable for the formation of mixed carboxyl/carbonic anhydrides, such as carbonyldiimidazole (CDI), isobutyl or ethyl chloroformate, frequently in the presence of a base such as those described above. Suitable solvents include, but are not limited to, CH₂Cl₂, THF, or CH₃CN. Another approach commonly used by those skilled in the art when X is OH is to treat the compound of Formula B, R²CO₂H, with a carboxylic acid chloride, for example such as Me₃CCOCl, in the presence of a base such as described above to generate a mixed carboxylic anhydride of the formula R²C(O)O(O)CCMe₃. Suitable solvents for carrying out the mixed anhydride reaction include, but are not limited to, aprotic solvents such as CH₂Cl₂, THF, or CH₃CN. In many cases it is possible to use a symmetric anhydride of the desired carboxylic acid of Formula B to effect the reaction of Scheme 1, optionally in the presence of a base such as described above, in which case X is O(O)CR² and the compound of Formula B is therefore R²C(O)O(O)R². Suitable solvents include, but are not limited to, CH₂Cl₂, THF, or CH₃CN. One skilled in the art will appreciate that in the event that the compound of Formula A has R¹ being H, the above transformations may afford a product compound of Formula 1 in which R¹ may be H and/or may be RC(O), depending upon the selection of reaction parameters such as time, temperature, solvent, and equivalents of the compound of Formula B employed.

-continued

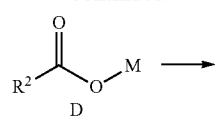

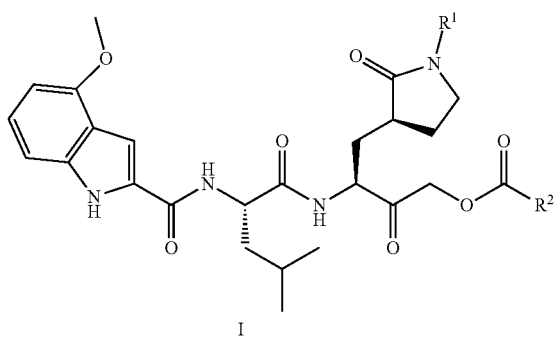

Scheme 2 illustrates a synthetic sequence for the preparation of compounds of Formula I as shown, wherein a compound of Formula C (PCT Published Application Number WO 2005/113580) is treated with a compound of Formula D. In this embodiment, X is typically a halogen, most frequently Cl, Br, or I and the compound of Formula C is an α-halo ketone. One skilled in the art will recognize that the compound of Formula B is a salt of the carboxylic acid R²CO₂H. The M in the compound of Formula B may be an ion of a metallic element, such as an alkali metal or an alkaline earth metal, or M may represent an ammonium ion such as a tetraalkylammonium ion or a diisopropylethylammonium ion, for example. Such carboxylic acid salts may be intentionally prepared before the synthetic reaction is conducted, or alternatively they may be prepared in the reaction mixture. Suitable solvents include, but are not limited to, DMF, THF, acetone, or CH₃CN. One skilled in the art will appreciate that it is possible to prepare compounds of the present invention in which R¹ may be some group other than H.

The following schemes 3-7 illustrate, in a non-limiting manner, how such other R¹ groups may be introduced to provide compounds of Formula A, and to provide ultimately compounds of the present invention of Formula I, in which R¹ is not equal to H.

Scheme 2

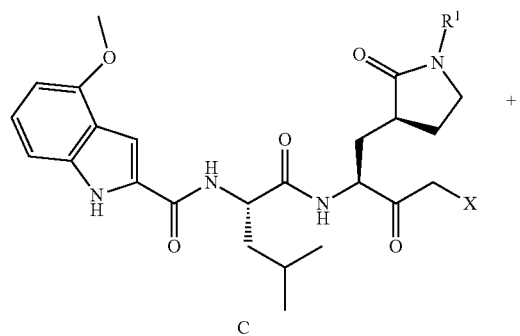

Scheme 3

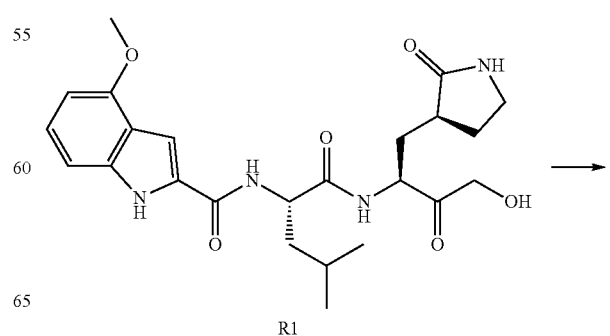

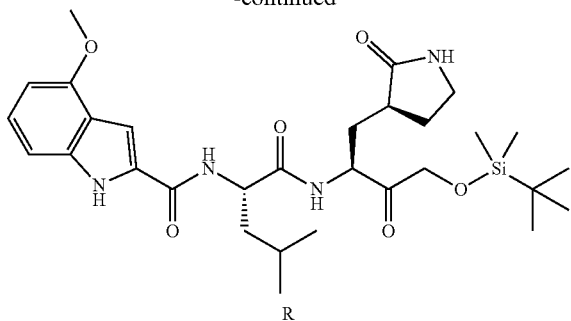

R

Scheme 3 illustrates a synthetic sequence for the preparation of compounds of Formula R as shown, wherein the compound of Formula R1 (see WO 2005/113580) is treated with a reagent that silylates the OH group as shown. Such methods are well known to those skilled in the art, and the reaction illustrated may be accomplished by exposure of the compound of Formula R1 to tert-butyldimethylchlorosilane, for example, typically in the presence of imidazole. Suitable solvents include, but are not limited to, $CH_2Cl_2$, DMF, THF, or $CH_3CN$. One skilled in the art will appreciate that other reagents may be used to introduce the tert-butyldimethylsilyl (TBDMS) group, and that other silyl ethers closely similar to compounds of Formula R may be prepared by the selection of other appropriate silylating agents, for example triisopropylsilyl (TIPS) or tert-butyldiphenylsilyl (TBDPS) ethers.

Scheme 4

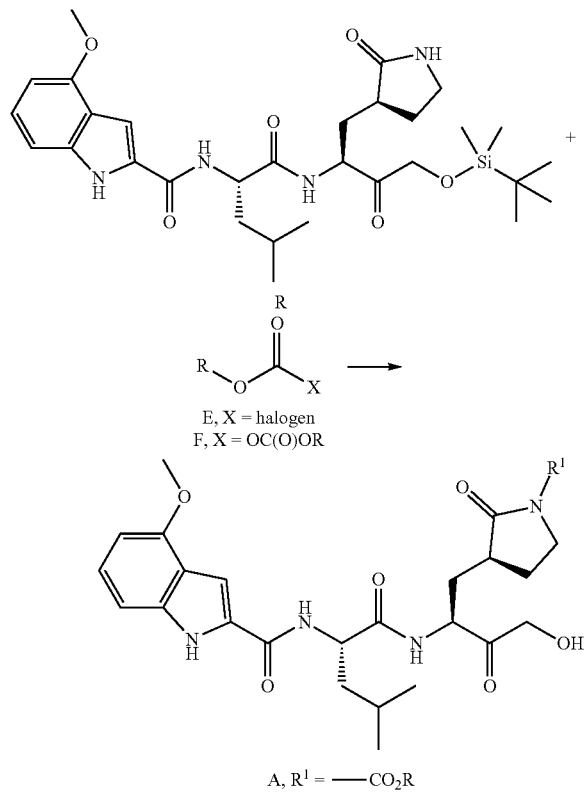

E, X = halogen
F, X = OC(O)OR

A, $R^1$ = —CO$_2$R

Scheme 4 illustrates a synthetic sequence for the preparation of compounds of Formula A as shown, wherein the compound of Formula R is transformed, typically in two synthetic manipulations, into the compound of Formula A in which $R^1$ is equal to —C(O)OR as illustrated. In the first manipulation, the compound of Formula R may be treated with a compound of Formula E as shown, wherein X is a halogen atom, most frequently chlorine. In this case the compound of Formula E is known as a chloroformate, and such methods are well known to those skilled in the art. The reaction is conducted in the presence of a suitable base to consume the hydrogen halide HX produced as a by-product of the reaction. Examples of suitable bases include, but are not limited to, tertiary amines such as N-methyl morpholine (NMM), 2,6-dimethylpyridine, or diisopropylethylamine (DIEA), or inorganic bases such as magnesium oxide (MgO), sodium carbonate ($Na_2CO_3$), or potassium bicarbonate ($KHCO_3$). Suitable solvents include, but are not limited to, $CH_2Cl_2$, THF, or $CH_3CN$. Alternatively, in the first manipulation, the compound of Formula R may be treated with a compound of Formula F as shown, frequently known as a pyrocarbonate by those skilled in the art. The reaction is frequently conducted in the presence of a nucleophilic catalyst to accelerate the reaction. Examples of such nucleophilic catalysts include, but are not limited to, 4-(dimethylamino)pyridine, imidazole, or 1,8-Diazabicyclo[5.4.0]undec-7-ene (DBU). Suitable solvents include, but are not limited to, $CH_2Cl_2$, THF, pyridine, or $CH_3CN$. In the second manipulation, the silyl ether may be removed to afford the compounds of Formula A as shown. One skilled in the art will understand that the selection of reagents and conditions to effect this transformation will depend upon the nature of the particular C(O)OR group introduced at the first manipulation, such that the conditions for the second manipulation are not incompatible with the integrity of the C(O)OR group introduced at the first manipulation. Commonly employed conditions for removal of the silyl ether include exposure to acids, such as trifluoroacetic acid (TFA), acetic acid (AcOH), hydrofluoric (HF), or hydrochloric (HCl) acid, for example, or alternately exposure to a source of fluoride ion, with tetrabutylammonium fluoride (TBAF) being especially commonly used. One skilled in the art will appreciate that the selection of suitable solvents for the second manipulation will depend upon the reagents selected to effect that transformation and may include, but are not limited to, $CH_2Cl_2$, THF, or $CH_3CN$. It is to be understood that the hydroxy ketone compound of Formula A can be further reacted to introduce the —C(O)$R^2$ moiety as previously described above in Schemes 1 and 2 to provide compounds of Formula I.

Scheme 5

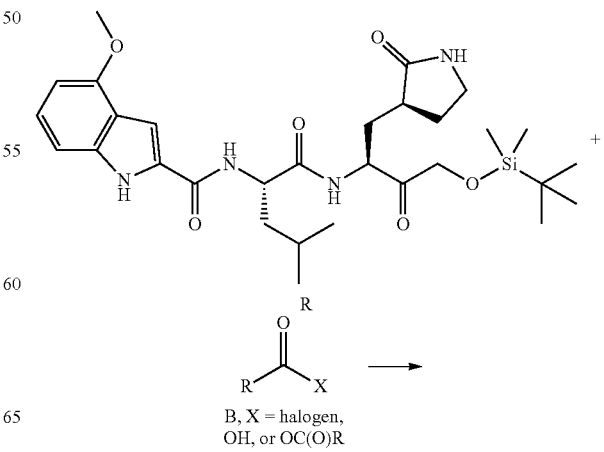

B, X = halogen,
OH, or OC(O)R

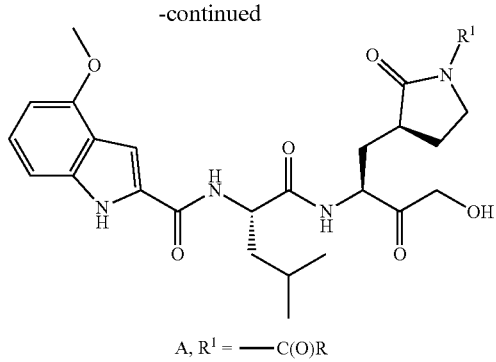

A, R$^1$ = —C(O)R

Scheme 5 illustrates a synthetic sequence for the preparation of compounds of Formula A as shown, wherein the compound of Formula R is transformed, typically in two synthetic manipulations, into the compound of Formula A in which R$^1$ is equal to —C(O)R as illustrated. In the first manipulation, the compound of Formula R is treated with a compound of Formula B as shown, wherein X is typically a halogen atom or OH. Such methods are well known to those skilled in the art. For example, when X is a halogen atom, the reaction is conducted in the presence of a base to consume the hydrogen halide HX produced as a by-product of the reaction. Examples of suitable bases include, but are not limited to, tertiary amines such as NMM, 2,6-dimethylpyridine, or DIEA, or inorganic bases such as MgO, Na$_2$CO$_3$, or KHCO$_3$. Suitable solvents include, but are not limited to, CH$_2$Cl$_2$, DMF, THF, or CH$_3$CN. When X is OH, the compound B is a carboxylic acid and it is customary to use a reagent or combination of reagents to accelerate the reaction of the carboxylic acid B. One skilled in the art may choose to use, for example, a carbodiimide reagent such as EDC or DCC, optionally in the presence of an auxiliary nucleophile such as HOBt or HOPO. Further, when X is OH, one skilled in the art may choose to use reagents that are suitable for the formation of mixed carboxyl/carbonic anhydrides, such as CDI, isobutyl or ethyl chloroformate, frequently in the presence of a base such as described above. Suitable solvents include, but are not limited to, CH$_2$Cl$_2$, THF or CH$_3$CN. Another approach commonly used by those skilled in the art when X═OH is to treat the compound of Formula B with a carboxylic acid chloride, for example such as Me$_3$CCOCl, in the presence of a base such as described above to generate a mixed carboxylic anhydride of the Formula RC(O)O(O)CCMe$_3$. Suitable solvents include, but are not limited to, CH$_2$Cl$_2$, THF or CH$_3$CN. In many cases it is possible to use a symmetric anhydride of the desired carboxylic acid of Formula B to effect the reaction of Scheme 5, optionally in the presence of a base such as described above, in which case X═O(O)CR and the compound of Formula B is therefore RC(O)O(O)R. Suitable solvents include, but are not limited to, CH$_2$Cl$_2$, THF or CH$_3$CN.

In the second manipulation, the silyl ether may be removed to afford the compounds of Formula A as shown. One skilled in the art will understand that the selection of reagents and conditions to effect this transformation will depend upon the nature of the particular C(O)R group introduced at the first manipulation, such that the conditions for the second manipulation are not incompatible with the integrity of the C(O)R group introduced at the first manipulation. Commonly employed conditions for removal of the silyl ether include exposure to acids, such as trifluoroacetic acid, acetic acid, hydrofluoric, or hydrochloric acid, for example, or alternately exposure to a source of fluoride ion, with tetrabutylammonium fluoride being especially commonly used. One skilled in the art will appreciate that the selection of suitable solvents for the second manipulation will depend upon the reagents selected to effect that transformation and may include, but are not limited to, CH$_2$Cl$_2$, THF or CH$_3$CN. It is to be understood that the hydroxy ketone compound of Formula A can be further reacted to introduce the —C(O)R$^2$ moiety as previously described above in Schemes 1 and 2 to provide compounds of Formula I.

Scheme 6

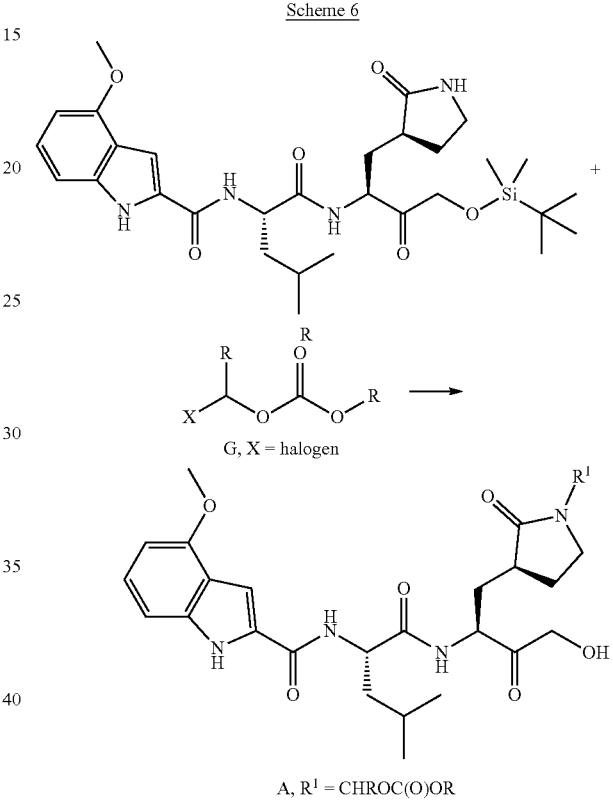

A, R$^1$ = CHROC(O)OR

Scheme 6 illustrates a synthetic sequence for the preparation of compounds of Formula A as shown, wherein the compound of Formula R is transformed, typically in two synthetic manipulations, into the compound of Formula A in which R$^1$ is equal to —CHR'OC(O)OR as illustrated. In the first manipulation, the compound of Formula R may be treated with a compound of Formula G in which R' may include H and X is a halogen atom. Such compounds of Formula G are described in the chemical literature and may be commercially available. The reaction is affected by treatment with a base, for example potassium t-butoxide (KOtBu) or cesium carbonate (Cs$_2$CO$_3$), in a suitable solvent which may include, but is not limited to, THF, DMF, DMSO or CH$_3$CN.

In the second manipulation, the silyl ether may be removed to afford the compounds of Formula A as shown. One skilled in the art will understand that the selection of reagents and conditions to effect this transformation may depend upon the nature of the particular CHR'OC(O)OR group introduced at the first manipulation, such that the conditions for the second manipulation are not incompatible with the integrity of the CHR'OC(O)OR group introduced at the first manipulation.

The silyl ether may be removed by exposure to a source of fluoride ion, with tetrabutylammonium fluoride being especially suitable. Suitable solvents for the second manipulation may include, but are not limited to, DMF, $CH_2Cl_2$, THF or $CH_3CN$. It is to be understood that the hydroxy ketone compound of Formula A can be further reacted to introduce the $—C(O)R^2$ moiety as previously described above in Schemes 1 and 2 to provide compounds of Formula I.

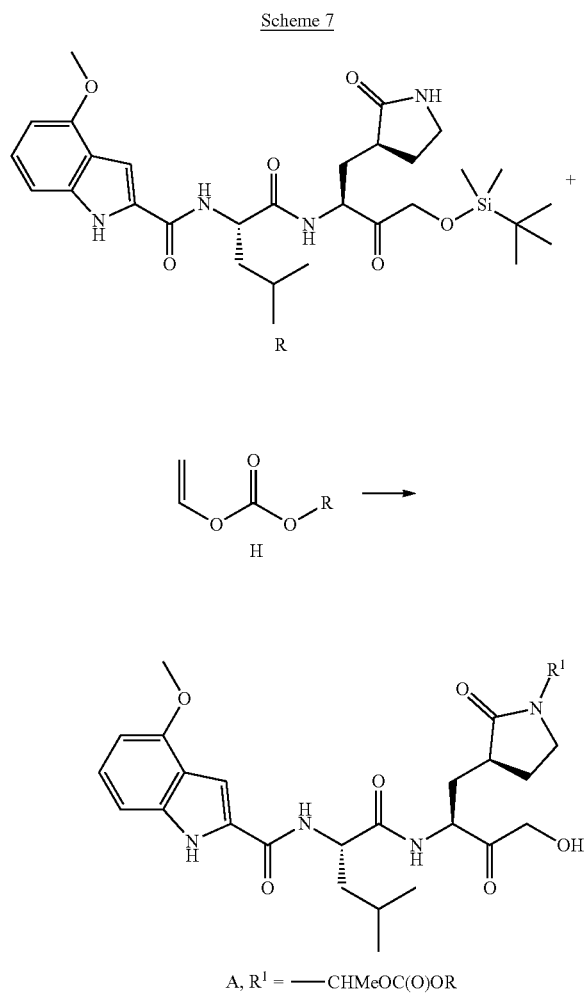

Scheme 7

A, $R^1$ = —CHMeOC(O)OR

Scheme 7 illustrates a synthetic sequence for the preparation of compounds of Formula A as shown, wherein the compound of Formula R is transformed, typically in two synthetic manipulations, into the compound of Formula A in which $R^1$ is equal to —CHR'OC(O)OR as illustrated. In the first manipulation, the compound of Formula R may be treated with an olefinic compound of Formula H ($H_2C$=CHOC(O)OR, Scheme 7) in which R may not include H. Such compounds of Formula H are described in the chemical literature and may be commercially available. The reaction is affected by treatment with a catalyst as known to those skilled in the art, which may include but is not limited to an acid, a compound of palladium, or a compound of mercury. Suitable solvents may include, but are not limited to, $CH_2Cl_2$, THF or $CH_3CN$.

In the second manipulation, the silyl ether may be removed to afford the compounds of Formula A as shown. One skilled in the art will understand that the selection of reagents and conditions to effect this transformation may depend upon the nature of the particular CHROC(O)OR group introduced at the first manipulation, such that the conditions for the second manipulation are not incompatible with the integrity of the —CHR'OC(O)OR group introduced at the first manipulation. The silyl ether may be removed by exposure to a source of fluoride ion, with tetrabutylammonium fluoride being especially suitable. Suitable solvents for the second manipulation may include, but are not limited to, DMF, $CH_2Cl_2$, THF or $CH_3CN$. It is to be understood that the hydroxy ketone compound of Formula A can then be further reacted to introduce the $—C(O)R^2$ moiety as previously described above in Schemes 1 and 2 to provide compounds of Formula I.

Examples

The following Examples can be prepared according to the methods described in Schemes 1-7 hereinabove.

Example 1: (3S)-4-[(3S)-1-acetyl-2-oxopyrrolidin-3-yl]-3-({N-[(4-methoxy-1H-indol-2-yl)carbonyl]-L-leucyl}amino)-2-oxobutyl 2,6-dimethylbenzoate Example 2: methyl (3S)-3-[(2S)-4-[(2,6-dimethylbenzoyl)oxy]-2-({N-[(4-methoxy-1H-indol-2-yl)carbonyl]-L-leucyl}amino)-3-oxobutyl]-2-oxopyrrolidine-1-carboxylate Example 3: (3S)-4-[(3S)-1-{(1S)-1-[(methoxycarbonyl)oxy]ethyl}-2-oxopyrrolidin-3-yl]-3-({N-[(4-methoxy-1H-indol-2-yl)carbonyl]-L-leucyl}amino)-2-oxobutyl 2,6-dimethyl benzoate Example 4: (3S)-3-({N-[(4-methoxy-1H-indol-2-yl)carbonyl]-L-leucyl}amino)-2-oxo-4-[(3S)-2-oxopyrrolidin-3-yl]butyl N,N-dimethylglycinate, trifluoroacetate salt LCMS m/z 558.3 [M+H]$^+$. Retention time: 2.00 minutes (Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 5: (3S)-3-({N-[(4-methoxy-1H-indol-2-yl)carbonyl]-L-leucyl}amino)-2-oxo-4-[(3S)-2-oxopyrrolidin-3-yl]butyl N,N-dimethyl-D-alaninate Example 6: (3S)-3-({N-[(4-methoxy-1H-indol-2-yl)carbonyl]-L-leucyl}amino)-2-oxo-4-[(3S)-2-oxopyrrolidin-3-yl]butyl N,N,2-trimethylalaninate Example 7: (3S)-3-({N-[(4-methoxy-1H-indol-2-yl)carbonyl]-L-leucyl}amino)-2-oxo-4-[(3S)-2-oxopyrrolidin-3-yl]butyl 4-(dimethylamino)-2,2-dimethyl butanoate Example 8: (3S)-3-({N-[(4-methoxy-1H-indol-2-yl)carbonyl]-L-leucyl}amino)-2-oxo-4-[(3S)-2-oxopyrrolidin-3-yl]butyl 4-(dimethylamino)butanoate Example 9: (3S)-3-({N-[(4-methoxy-1H-indol-2-yl)carbonyl]-L-leucyl}amino)-2-oxo-4-[(3S)-2-oxopyrrolidin-3-yl]butyl propanoate LCMS m/z 529.3 [M+H]$^+$. $^1$H NMR (400 MHz, chloroform-d) δ 9.71 (br s, 1H), 8.79 (d, J=5.9 Hz, 1H), 7.17 (dd, J=8, 8 Hz, 1H), 7.11 (br d, J=2 Hz, 1H), 6.99 (d, J=8.3 Hz, 1H), 6.94 (br d, J=8.2 Hz, 1H), 6.47 (d, J=7.7 Hz, 1H), 6.24 (br s, 1H), 4.88 (AB quartet, $J_{AB}$=17.1 Hz, $\Delta V_{AB}$=55.3 Hz, 2H), 4.83-4.74 (m, 1H), 4.53-4.44 (m, 1H), 3.92 (s, 3H), 3.28-3.13 (m, 2H), 2.46-2.34 (m, 1H), 2.43 (q, J=7.6 Hz, 2H), 2.32-2.21 (m, 1H), 2.06 (ddd, J=14.5, 10.9, 7.2 Hz, 1H), 1.92-1.63 (m, 5H, assumed; partially obscured by water peak), 1.15 (t, J=7.5 Hz, 3H), 0.97 (br d, J=6 Hz, 6H).

Example 10: (3S)-3-({N-[(4-methoxy-1H-indol-2-yl)carbonyl]-L-leucyl}amino)-2-oxo-4-[(3S)-2-oxopyrrolidin-3-yl]butyl 2-methylpropanoate LCMS m/z 543.2 [M+H]$^+$. $^1$H NMR (400 MHz, chloroform-d) δ 9.30 (br s, 1H), 8.82 (br d, J=5.3 Hz, 1H), 7.19 (dd, J=8, 8 Hz, 1H), 7.13-7.10 (m, 1H), 7.01 (d, J=8.4 Hz, 1H), 6.73 (br d, J=8 Hz, 1H), 6.50 (d, J=7.7 Hz, 1H), 5.82 (br s, 1H), 4.86 (AB quartet, J$_{AB}$=17.0 Hz, ΔV$_{AB}$=52.1 Hz, 2H), 4.82-4.72 (m, 1H), 4.50-4.40 (m, 1H), 3.94 (s, 3H), 3.38-3.24 (m, 2H), 2.66 (heptet, J=7.0 Hz, 1H), 2.50-2.30 (m, 2H), 2.14-2.01 (m, 1H), 1.99-1.89 (m, 1H), 1.89-1.6 (m, 4H, assumed; partially obscured by water peak), 1.21 (d, J=7.0 Hz, 6H), 0.99 (d, J=6 Hz, 3H), 0.98 (d, J=6 Hz, 3H).

Example 11: (3S)-3-({N-[(4-methoxy-1H-indol-2-yl)carbonyl]-L-leucyl}amino)-2-oxo-4-[(3S)-2-oxopyrrolidin-3-yl]butyl 2-methylbenzoate LCMS m/z 591.6 [M+H]$^+$. By $^1$H NMR, this material comprised a mixture of rotamers. $^1$H NMR (400 MHz, methanol-d$_4$) δ 7.96-7.90 (m, 1H), 7.47-7.40 (m, 1H), 7.31-7.22 (m, 3H), 7.14 (br dd, J=8, 8 Hz, 1H), 7.02 (br d, J=8 Hz, 1H), 6.51 (br d, J=8 Hz, 1H), [5.21 (d, half of AB quartet, J=17.1 Hz) and 5.16-5.07 (m), total 2H], [4.83-4.78 (m) and 4.76-4.58 (m), total 2H], [3.93 (s) and 3.92 (s), total 3H], 3.31-3.21 (m, 2H, assumed; partially obscured by solvent peak), [2.62-2.49 (m), 2.49-2.25 (m), and 2.20-2.09 (m), total 3H], [2.54 (s) and 2.54 (s), total 3H], 1.95-1.69 (m, 5H), 1.06-1.01 (m, 3H), 1.01-0.97 (m, 3H).

Example 12: (3S)-3-({N-[(4-methoxy-1H-indol-2-yl)carbonyl]-L-leucyl}amino)-2-oxo-4-[(3S)-2-oxopyrrolidin-3-yl]butyl cyclohexanecarboxylate LCMS m/z 583.3 [M+H]$^+$. Retention time: 3.12 minutes (Analytical conditions identical to those described in Example 4).

Example 13: (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclohexanecarboxylate LCMS m/z 597.6 [M+H]$^+$. Retention time: 3.23 minutes (Analytical conditions identical to those described in Example 4).

Example 14: (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclobutanecarboxylate LCMS m/z 569.3 [M+H]$^+$. Retention time: 3.00 minutes (Analytical conditions identical to those described in Example 4).

Example 15: (3S)-3-({N-[(4-methoxy-1H-indol-2-yl)carbonyl]-L-leucyl}amino)-2-oxo-4-[(3S)-2-oxopyrrolidin-3-yl]butyl 2-methoxybenzoate LCMS m/z 607.5 [M+H]$^+$. Retention time: 2.63 minutes (Analytical conditions identical to those described in Example 4, except that the analysis was carried out at 60° C.).

Example 16: (3S)-3-({N-[(4-methoxy-1H-indol-2-yl)carbonyl]-L-leucyl}amino)-2-oxo-4-[(3S)-2-oxopyrrolidin-3-yl]butyl 2-chlorobenzoate LCMS m/z 611.5 [M+H]$^+$. Retention time: 2.77 minutes (Analytical conditions identical to those described in Example 4, except that the analysis was carried out at 60° C.).

Example 17: (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethylpiperidine-4-carboxylate, trifluoroacetate salt LCMS m/z 612.6 [M+H]$^+$. Retention time: 2.12 minutes (Analytical conditions identical to those described in Example 4).

Example 18: (3S)-3-({N-[(4-methoxy-1H-indol-2-yl)carbonyl]-L-leucyl}amino)-2-oxo-4-[(3S)-2-oxopyrrolidin-3-yl]butyl (2S)-2-methylbutanoate LCMS m/z 557.7 [M+H]$^+$. Retention time: 2.91 minutes (Analytical conditions identical to those described in Example 4).

Example 19: (3S)-3-({N-[(4-methoxy-1H-indol-2-yl)carbonyl]-L-leucyl}amino)-2-oxo-4-[(3S)-2-oxopyrrolidin-3-yl]butyl (2R)-2-methylbutanoate LCMS m/z 557.7 [M+H]$^+$. Retention time: 2.91 minutes (Analytical conditions identical to those described in Example 4).

Example 20: (3S)-3-({N-[(4-methoxy-1H-indol-2-yl)carbonyl]-L-leucyl}amino)-2-oxo-4-[(3S)-2-oxopyrrolidin-3-yl]butyl bicyclo[1.1.1]pentane-1-carboxylate Example 21: (3S)-3-({N-[(4-methoxy-1H-indol-2-yl)carbonyl]-L-leucyl}amino)-2-oxo-4-[(3S)-2-oxopyrrolidin-3-yl]butyl 1-methylcyclopropanecarboxylate LCMS m/z 555.3 [M+H]$^+$. Retention time: 2.85 minutes (Analytical conditions identical to those described in Example 4).

Example 22: (3S)-3-({N-[(4-methoxy-1H-indol-2-yl)carbonyl]-L-leucyl}amino)-2-oxo-4-[(3S)-2-oxopyrrolidin-3-yl]butyl 1,3-dimethylazetidine-3-carboxylate Example 23: (3S)-3-({N-[(4-methoxy-1H-indol-2-yl)carbonyl]-L-leucyl}amino)-2-oxo-4-[(3S)-2-oxopyrrolidin-3-yl]butyl 4-methylpyridine-3-carboxylate, trifluoroacetate salt LCMS m/z 592.5 [M+H]$^+$. Retention time: 2.10 minutes (Analytical conditions identical to those described in Example 4, except that the analysis was carried out at 60° C.).

Example 24: (3S)-3-({N-[(4-methoxy-1H-indol-2-yl)carbonyl]-L-leucyl}amino)-2-oxo-4-[(3S)-2-oxopyrrolidin-3-yl]butyl 2-methylpyridine-3-carboxylate, trifluoroacetate salt LCMS m/z 592.5 [M+H]$^+$. Retention time: 2.04 minutes (Analytical conditions identical to those described in Example 4, except that the analysis was carried out at 60° C.).

Example 25: (3S)-3-({N-[(4-methoxy-1H-indol-2-yl)carbonyl]-L-leucyl}amino)-2-oxo-4-[(3S)-2-oxopyrrolidin-3-yl]butyl (3R)-1-methylpyrrolidine-3-carboxylate Example 26: (3S)-3-({N-[(4-methoxy-1H-indol-2-yl)carbonyl]-L-leucyl}amino)-2-oxo-4-[(3S)-2-oxopyrrolidin-3-yl]butyl (3S)-1-methylpyrrolidine-3-carboxylate Example 27: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-D-prolinate, trifluoroacetate salt

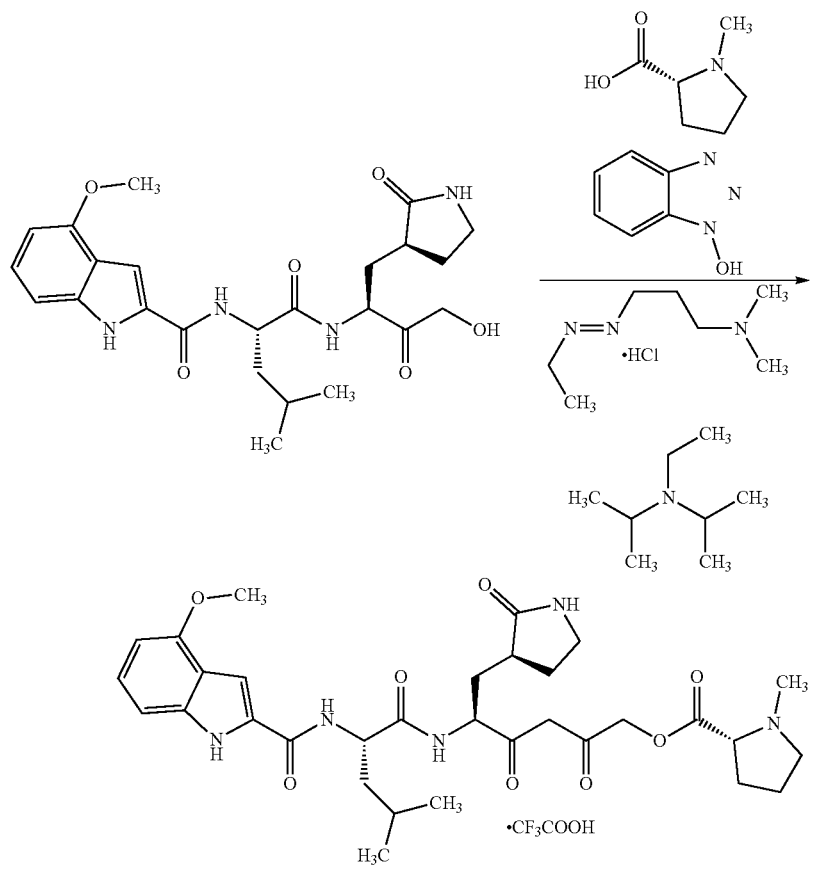

This reaction was carried out in library format.

Stock solutions were prepared as follows: N-[(2S)-1-({(2S)-4-hydroxy-3-oxo-1-[(3S)-2-oxopyrrolidin-3-yl]butan-2-yl}amino)-4-methyl-1-oxopentan-2-yl]-4-methoxy-1H-indole-2-carboxamide (320 mg, 0.677 mmol) was dissolved in N,N-dimethylformamide (1.8 mL); 1H-benzotriazol-1-ol (113 mg, 0.836 mmol) was dissolved in N,N-dimethylformamide (1.8 mL); and N,N-diisopropylethylamine (333 μL, 1.91 mmol) and 1-[3-(dimethylamino)propyl]-3-ethylcarbodiimide hydrochloride (130 mg, 0.678 mmol) were dissolved in N,N-dimethylformamide (3.6 mL).

Into a reaction vial were placed the following: stock solution of N-[(2S)-1-({(2S)-4-hydroxy-3-oxo-1-[(3S)-2-oxopyrrolidin-3-yl]butan-2-yl}amino)-4-methyl-1-oxopentan-2-yl]-4-methoxy-1H-indole-2-carboxamide (0.1 mL, 40 μmol), stock solution of 1H-benzotriazol-1-ol (100 μL, 46 μmol), and stock solution of N,N-diisopropylethylamine and 1-[3-(dimethylamino)propyl]-3-ethylcarbodiimide hydrochloride (218 μL, 0.116 mmol of N,N-diisopropylethylamine and 41.0 pmol of 1-[3-(dimethylamino)propyl]-3-ethylcarbodiimide hydrochloride). To this was added 1-methyl-D-proline (6.46 mg, 50.0 μmol), and the reaction mixture was stirred for 3 days. After removal of volatiles using a Genevac evaporator, the residue was purified via reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 8.54 minutes, followed by 95% B for 1.46 minutes; Flow rate: 25 mL/minute) to afford (3S)-3-({N-[(4-methoxy-1H-indol-2-yl)carbonyl]-L-leucyl}amino)-2-oxo-4-[(3S)-2-oxopyrrolidin-3-yl]butyl 1-methyl-D-prolinate, trifluoroacetate salt (Example 27). Yield: 3.0 mg, 5.1 μmol, 13%. LCMS m/z 584.3 [M+H]$^+$. Retention time: 2.06 minutes (Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

Example 28: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-L-prolinate, trifluoroacetate salt LCMS m/z 584.3 [M+H]$^+$. Retention time: 2.08 minutes (Analytical conditions identical to those described in Example 4).

Example 29: (3S)-3-({N-[(4-methoxy-1H-indol-2-yl)carbonyl]-L-leucyl}amino)-2-oxo-4-[(3S)-2-oxopyrrolidin-3-yl]butyl pyridine-3-carboxylate, trifluoroacetate salt LCMS m/z 578.2 [M+H]$^+$. Retention time: 2.35 minutes (Analytical conditions identical to those described in Example 4).

Example 30: (3S)-3-({N-[(4-methoxy-1H-indol-2-yl)carbonyl]-L-leucyl}amino)-2-oxo-4-[(3S)-2-oxopyrrolidin-3-yl]butyl 1-methylpiperidine-4-carboxylate, trifluoroacetate salt LCMS m/z 598.3 [M+H]$^+$. Retention time: 2.05 minutes (Analytical conditions identical to those described in Example 4).

Example 32: (3S)-3-({N-[(4-methoxy-1H-indol-2-yl)carbonyl]-L-leucyl}amino)-2-oxo-4-[(3S)-2-oxopyrrolidin-3-yl]butyl (2R)-4-methylmorpholine-2-carboxylate Example 33: (3S)-3-({N-[(4-methoxy-1H-indol-2-yl)carbonyl]-L-leucyl}amino)-2-oxo-4-[(3S)-2-oxopyrrolidin-3-yl]butyl (2S)-1-methylpiperidine-2-carboxylate Example 34: (3S)-3-({N-[(4-methoxy-1H-indol-2-yl)carbonyl]-L-leucyl}amino)-2-oxo-4-[(3S)-2-oxopyrrolidin-3-yl]butyl pyridine-4-carboxylate, trifluoroacetate salt mL/minute) then afforded (3S)-3-({N-[(4-methoxy-1H-indol-2-yl)carbonyl]-L-leucyl}amino)-2-oxo-4-[(3S)-2-oxopyrrolidin-3-yl]butyl pyridine-4-carboxylate, trifluoroacetate salt (Example 34). Yield: 8.5 mg, 15 μmol, 27%. LCMS m/z 578.5 [M+H]⁺. Retention time: 2.28 minutes (Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute).

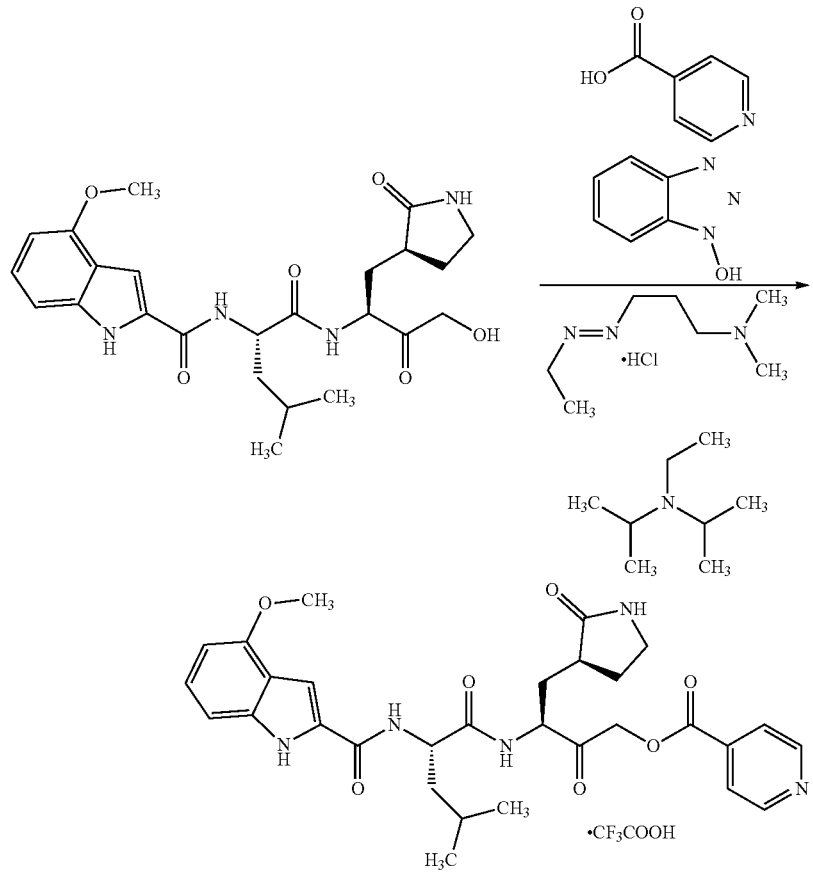

34

N,N-Diisopropylethylamine (27.7 μL, 0.159 mmol) was added to a mixture of pyridine-4-carboxylic acid (8.60 mg, 69.8 μmol), N-[(2S)-1-({(2S)-4-hydroxy-3-oxo-1-[(3S)-2-oxopyrrolidin-3-yl]butan-2-yl}amino)-4-methyl-1-oxopentan-2-yl]-4-methoxy-1H-indole-2-carboxamide (30 mg, 63 μmol), 1-[3-(dimethylamino)propyl]-3-ethylcarbodiimide hydrochloride (10.8 mg, 56.3 μmol), and 1H-benzotriazol-1-ol (9.44 mg, 69.8 μmol) in N,N-dimethylformamide (0.4 mL). After the reaction mixture had been stirred at room temperature for two days, volatiles were removed using a Genevac evaporator; reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 25% to 65% B over 8.5 minutes, then 65% to 95% B over 0.5 minutes, then 95% B for 1.0 minute; Flow rate: 25

Example 35: (3S)-3-({N-[(4-methoxy-1H-indol-2-yl)carbonyl]-L-leucyl}amino)-2-oxo-4-[(3S)-2-oxopyrrolidin-3-yl]butyl pyridine-2-carboxylate LCMS m/z 578.2 [M+H]⁺. Retention time: 2.50 minutes (Analytical conditions identical to those described in Example 4).

Example 36: (3S)-3-({N-[(4-methoxy-1H-indol-2-yl)carbonyl]-L-leucyl}amino)-2-oxo-4-[(3S)-2-oxopyrrolidin-3-yl]butyl (2S)-4-methylmorpholine-2-carboxylate Example 37: (3S)-3-({N-[(4-methoxy-1H-indol-2-yl)carbonyl]-L-leucyl}amino)-2-oxo-4-[(3S)-2-oxopyrrolidin-3-yl]butyl (2R)-1-methylpiperidine-2-carboxylate, trifluoroacetate salt LCMS m/z 598.3 [M+H]⁺. Retention time: 2.09 minutes (Analytical conditions identical to those described in Example 4).

Example 38: (3S)-3-({N-[(4-methoxy-1H-indol-2-yl)carbonyl]-L-leucyl}amino)-2-oxo-4-[(3S)-2-oxopyrrolidin-3-yl]butyl L-valinate Example 39: (3S)-3-({N-[(4-methoxy-1H-indol-2-yl)carbonyl]-L-leucyl}amino)-2-oxo-4-[(3S)-2-oxopyrrolidin-3-yl]butyl 1,3-dimethyl-1H-pyrazole-4-carboxylate LCMS m/z 595.2 [M+H]⁺. Retention time: 2.33 minutes (Analytical conditions identical to those described in Example 4, except that the analysis was carried out at 80° C.).

Example 40: (3S)-3-({N-[(4-methoxy-1H-indol-2-yl)carbonyl]-L-leucyl}amino)-2-oxo-4-[(3S)-2-oxopyrrolidin-3-yl]butyl 1,5-dimethyl-1H-imidazole-4-carboxylate, trifluoroacetate salt LCMS m/z 595.5 [M+H]⁺. By $^1$H NMR, this material comprised a mixture of rotamers. $^1$H NMR (500 MHz, DMSO-d$_6$), characteristic peaks, integrations are approximate: δ 7.10 (dd, J=8, 8 Hz, 1H), 7.03-6.98 (m, 1H), 6.53-6.49 (m, 1H), 4.65-4.39 (m, 2H), 3.88 (s, 3H), [3.67 (s) and 3.67 (s), total 3H], 3.20-3.05 (m, 2H), [2.48 (br s) and 2.48 (s), total 3H], 2.39-1.98 (m, 3H), 1.81-1.50 (m, 5H), 0.95 (br d, J=6.2 Hz, 3H), 0.90 (br d, J=6.2 Hz, 3H). Retention time: 1.86 minutes (Analytical conditions. Column: Waters Sunfire C18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, followed by 95% B for 1.0 minute; Flow rate: 2 mL/minute).

Example 41: (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethyl-1H-imidazole-5-carboxylate Example 42: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-pyrazole-5-carboxylate LCMS m/z 581.5 [M+H]⁺. Retention time: 2.43 minutes (Analytical conditions identical to those described in Example 4, except that the analysis was carried out at 60° C.).

Example 43: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-pyrazole-3-carboxylate LCMS m/z 581.2 [M+H]⁺. Retention time: 2.26 minutes (Analytical conditions identical to those described in Example 4, except that the analysis was carried out at 80° C.).

Example 44: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-pyrazole-4-carboxylate LCMS m/z 581.2 [M+H]⁺. Retention time: 2.25 minutes (Analytical conditions identical to those described in Example 4, except that the analysis was carried out at 80° C.).

Example 45: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-5-carboxylate, trifluoroacetate salt LCMS m/z 581.2 [M+H]⁺. Retention time: 1.84 minutes (Analytical conditions identical to those described in Example 4, except that the analysis was carried out at 80° C.).

Example 46: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-2-carboxylate Example 47: (3S)-3-({N-[(4-methoxy-1H-indol-2-yl)carbonyl]-L-leucyl}amino)-2-oxo-4-[(3S)-2-oxopyrrolidin-3-yl]butyl 4-methoxy-1-methyl-1H-imidazole-5-carboxylate Example 48: (3S)-3-({N-[(4-methoxy-1H-indol-2-yl)carbonyl]-L-leucyl}amino)-2-oxo-4-[(3S)-2-oxopyrrolidin-3-yl]butyl 1,3,5-trimethyl-1H-pyrazole-4-carboxylate LCMS m/z 609.3 [M+H]⁺. Retention time: 2.39 minutes (Analytical conditions identical to those described in Example 4, except that the analysis was carried out at 80° C.).

Example 49: (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethyl-1H-pyrazole-5-carboxylate Example 50: (3S)-3-({N-[(4-methoxy-1H-indol-2-yl)carbonyl]-L-leucyl}amino)-2-oxo-4-[(3S)-2-oxopyrrolidin-3-yl]butyl 1,4-dimethyl-1H-pyrazole-3-carboxylate Example 51: (3S)-3-({N-[(4-methoxy-1H-indol-2-yl)carbonyl]-L-leucyl}amino)-2-oxo-4-[(3S)-2-oxopyrrolidin-3-yl]butyl 1-methyl-1H-imidazole-4-carboxylate, trifluoroacetate salt LCMS m/z 581.2 [M+H]⁺. Retention time: 1.92 minutes (Analytical conditions identical to those described in Example 4, except that the analysis was carried out at 80° C.).

Example 52: (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)benzoate Example 53: (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]benzoate, trifluoroacetate salt LCMS m/z 634.3 [M+H]⁺. Retention time: 1.99 minutes (Analytical conditions identical to those described in Example 4, except that the analysis was carried out at 80° C.).

Example 54: (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]-6-methylbenzoate Example 55: (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)-6-methylbenzoate Example 56: (3S)-3-({N-[(4-methoxy-1H-indol-2-yl)carbonyl]-L-leucyl}amino)-2-oxo-4-[(3S)-2-oxopyrrolidin-3-yl]butyl 2-(methoxymethyl)-4-methylpyridine-3-carboxylate Example 57: (3S)-3-({N-[(4-methoxy-1H-indol-2-yl)carbonyl]-L-leucyl}amino)-2-oxo-4-[(3S)-2-oxopyrrolidin-3-yl]butyl 4-(methoxymethyl)-6-methylpyrimidine-5-carboxylate Example 58: (3S)-3-({N-[(4-methoxy-1H-indol-2-yl)carbonyl]-L-leucyl}amino)-2-oxo-4-[(3S)-2-oxopyrrolidin-3-yl]butyl 4-(methoxymethyl)-2-methylpyridine-3-carboxylate Example 59: (3S)-3-({N-[(4-methoxy-1H-indol-2-yl)carbonyl]-L-leucyl}amino)-2-oxo-4-[(3S)-2-oxopyrrolidin-3-yl]butyl 2-[(dimethylamino)methyl]-4-methylpyridine-3-carboxylate, trifluoroacetate salt LCMS m/z 649.6 [M+H]⁺. Retention time: 2.01 minutes (Analytical conditions identical to those described in Example 4, except that the analysis was carried out at 80° C.).

Example 60: (3S)-3-({N-[(4-methoxy-1H-indol-2-yl)carbonyl]-L-leucyl}amino)-2-oxo-4-[(3S)-2-oxopyrrolidin-3-yl]butyl 4-[(dimethylamino)methyl]-6-methylpyrimidine-5-carboxylate Example 61: (3S)-3-({N-[(4-methoxy-1H-indol-2-yl)carbonyl]-L-leucyl}amino)-2-oxo-4-[(3S)-2-oxopyrrolidin-3-yl]butyl 4-[(dimethylamino)methyl]-2-methylpyridine-3-carboxylate Example 62: (3S)-3-({N-[(4-methoxy-1H-indol-2-yl)carbonyl]-L-leucyl}amino)-2-oxo-4-[(3S)-2-oxopyrrolidin-3-yl]butyl 2,4-dimethylpyridine-3-carboxylate, trifluoroacetate salt LCMS m/z 606.2 [M+H]$^+$. Retention time: 1.94 minutes (Analytical conditions identical to those described in Example 4, except that the analysis was carried out at 80° C.).

Example 63: (3S)-3-({N-[(4-methoxy-1H-indol-2-yl)carbonyl]-L-leucyl}amino)-2-oxo-4-[(3S)-2-oxopyrrolidin-3-yl]butyl 4-methyl-2-(methylamino)pyridine-3-carboxylate Example 64: (3S)-3-({N-[(4-methoxy-1H-indol-2-yl)carbonyl]-L-leucyl}amino)-2-oxo-4-[(3S)-2-oxopyrrolidin-3-yl]butyl 2-ethoxy-4-methylpyridine-3-carboxylate, trifluoroacetate salt LCMS m/z 636.2 [M+H]$^+$. Retention time: 2.71 minutes (Analytical conditions identical to those described in Example 4, except that the analysis was carried out at 80° C.).

Example 65: (3S)-3-({N-[(4-methoxy-1H-indol-2-yl)carbonyl]-L-leucyl}amino)-2-oxo-4-[(3S)-2-oxopyrrolidin-3-yl]butyl 4-cyano-2,6-dimethylbenzoate LCMS m/z 630.2 [M+H]$^+$. Retention time: 2.74 minutes (Analytical conditions identical to those described in Example 4, except that the analysis was carried out at 80° C.).

Example 66: (3S)-3-({N-[(4-methoxy-1H-indol-2-yl)carbonyl]-L-leucyl}amino)-2-oxo-4-[(3S)-2-oxopyrrolidin-3-yl]butyl 2-methoxy-6-methylbenzoate LCMS m/z 621.5 [M+H]$^+$. Retention time: 2.97 minutes (Analytical conditions identical to those described in Example 4).

Example 67: (3S)-3-({N-[(4-methoxy-1H-indol-2-yl)carbonyl]-L-leucyl}amino)-2-oxo-4-[(3S)-2-oxopyrrolidin-3-yl]butyl 2-chloro-6-methyl benzoate LCMS m/z 625.2 (chlorine isotope pattern observed) [M+H]$^+$. Retention time: 2.81 minutes (Analytical conditions identical to those described in Example 4, except that the analysis was carried out at 80° C.).

Example 68: (3S)-3-({N-[(4-methoxy-1H-indol-2-yl)carbonyl]-L-leucyl}amino)-2-oxo-4-[(3S)-2-oxopyrrolidin-3-yl]butyl 3,5-di methylpyridine-4-carboxylate, trifluoroacetate salt LCMS m/z 606.2 [M+H]$^+$. Retention time: 2.03 minutes (Analytical conditions identical to those described in Example 4, except that the analysis was carried out at 80° C.).

Example 69: (3S)-3-({N-[(4-methoxy-1H-indol-2-yl)carbonyl]-L-leucyl}amino)-2-oxo-4-[(3S)-2-oxopyrrolidin-3-yl]butyl 4-chloro-2,6-dimethylbenzoate LCMS m/z 639.2 (chlorine isotope pattern observed) [M+H]$^+$. Retention time: 3.02 minutes (Analytical conditions identical to those described in Example 4, except that the analysis was carried out at 80° C.).

Example 70: (3S)-3-({N-[(4-methoxy-1H-indol-2-yl)carbonyl]-L-leucyl}amino)-2-oxo-4-[(3S)-2-oxopyrrolidin-3-yl]butyl 2,4,6-trimethylpyrimidine-5-carboxylate LCMS m/z 621.4 [M+H]$^+$. By $^1$H NMR, this material comprised a mixture of rotamers. $^1$H NMR (400 MHz, methanol-$d_4$), characteristic peaks, integrations are approximate: δ 7.29 (br d, J=5 Hz, 1H), 7.14 (br dd, J=8, 8 Hz, 1H), 7.01 (br d, J=8.3 Hz, 1H), 6.51 (d, J=7.7 Hz, 1H), [5.30 (d, half of AB quartet, J=17.2 Hz) and 5.23-5.14 (m), total 2H], 4.71-4.59 (m, 2H), 3.93 (br s, 3H), [2.63 (s) and 2.62 (s), total 3H], 2.56 (s, 3H), 2.53 (s, 3H), 2.38-2.26 (m, 1H), 2.22-2.10 (m, 1H), 1.96-1.68 (m, 5H), 1.04 (br d, J=6 Hz, 3H), 1.00 (d, J=6.1 Hz, 3H).

Example 71: (3S)-3-({N-[(4-methoxy-1H-indol-2-yl)carbonyl]-L-leucyl}amino)-2-oxo-4-[(3S)-2-oxopyrrolidin-3-yl]butyl 4,6-di methylpyrimidine-5-carboxylate LCMS m/z 607.4 [M+H]$^+$. $^1$H NMR (400 MHz, methanol-$d_4$) δ 8.91 (s, 1H), 7.29 (d, J=0.8 Hz, 1H), 7.14 (dd, J=8, 8 Hz, 1H), 7.02 (br d, J=8.3 Hz, 1H), 6.51 (d, J=7.7 Hz, 1H), 5.23 (AB quartet, $J_{AB}$=17.1 Hz, $\Delta V_{AB}$=6.3 Hz, 2H), 4.71-4.61 (m, 2H), 3.93 (s, 3H), 3.3-3.21 (m, 2H, assumed; partially obscured by solvent peak), 2.64-2.53 (m, 1H), 2.59 (s, 6H), 2.37-2.26 (m, 1H), 2.17 (ddd, J=14.2, 11.2, 4.9 Hz, 1H), 1.97-1.71 (m, 5H), 1.04 (d, J=6.0 Hz, 3H), 1.00 (d, J=6.0 Hz, 3H).

Example 72: (3S)-3-({N-[(4-methoxy-1H-indol-2-yl)carbonyl]-L-leucyl}amino)-2-oxo-4-[(3S)-2-oxopyrrolidin-3-yl]butyl 2-fluoro-6-methylbenzoate LCMS m/z 609.2 [M+H]$^+$. Retention time: 2.74 minutes (Analytical conditions identical to those described in Example 4, except that the analysis was carried out at 80° C.).

Example 73: (3S)-3-({N-[(4-methoxy-1H-indol-2-yl)carbonyl]-L-leucyl}amino)-2-oxo-4-[(3S)-2-oxopyrrolidin-3-yl]butyl 4-methoxy-2,6-dimethyl benzoate LCMS m/z 635.2 [M+H]$^+$. Retention time: 2.81 minutes (Analytical conditions identical to those described in Example 4, except that the analysis was carried out at 80° C.).

Example 74: (3S)-3-({N-[(4-methoxy-1H-indol-2-yl)carbonyl]-L-leucyl}amino)-2-oxo-4-[(3S)-2-oxopyrrolidin-3-yl]butyl 4-fluoro-2,6-dimethylbenzoate LCMS m/z 623.2 [M+H]$^+$. Retention time: 2.87 minutes (Analytical conditions identical to those described in Example 4, except that the analysis was carried out at 80° C.).

Example 75: (3S)-3-({N-[(4-methoxy-1H-indol-2-yl)carbonyl]-L-leucyl}amino)-2-oxo-4-[(3S)-2-oxopyrrolidin-3-yl]butyl 4,6-di methyl-2-(tetrahydro-2H-pyran-4-yl)pyrimidine-5-carboxylate LCMS m/z 691.3 [M+H]$^+$. Retention time: 2.60 minutes (Analytical conditions identical to those described in Example 4, except that the analysis was carried out at 80° C.).

Example 76: (3S)-3-({N-[(4-methoxy-1H-indol-2-yl)carbonyl]-L-leucyl}amino)-2-oxo-4-[(3S)-2-oxopyrrolidin-3-yl]butyl 3-fluoro-2,6-dimethylbenzoate Example 77: (3S)-3-({N-[(4-methoxy-1H-indol-2-yl)carbonyl]-L-leucyl}amino)-2-oxo-4-[(3S)-2-oxopyrrolidin-3-yl]butyl 3,5-dimethyl-1,2-oxazole-4-carboxylate Docking Experiments
Methods:
Homology Modeling. The sequence of 3C-like proteinase in SARS and COVID-19 can be found in references from the RCSB (e.g., 3IWM)[1] and the NCBI (e.g., Reference Sequence: YP_009725301.1 NCBI)[2].

```
SARS 3C Protease Sequence (PDB 3IWM):
SGFRKMAFPSGKVEGCMVQVTCGTTTLNGLWLDDTVYCPRHVICTAEDM

LNPNYEDLLIRKSNHSFLVQAGNVQLRVI

GHSMQNCLLRLKVDTSNPKTPKYKFVRIQPGQTFSVLACYNGSPSGVYQ

CAMRPNHTIKGSFLNGSCGSVGFNIDYDCV

SFCYMHHMELPTGVHAGTDLEGKFYGPFVDRQTAQAAGTDTTITLNVLA

WLYAAVINGDRWFLNRFTTTLNDFNLVA

MKYNYEPLTQDHVDILGPLSAQTGIAVLDMCAALKELLQNGMNGRTILG

STILEDEFTPFDVVRQCSGVTFQ

New Wuhan Coronavirus SARS-CoV-2 Sequence (same
section, 6Y84):
SGFRKMAFPSGKVEGCMVQVTCGTTTLNGLWLDDVVYCPRHVICTSEDM

LNPNYEDLLIRKSNHNFLVQAGNVQLRVI

GHSMQNCVLKLKVDTANPKTPKYKFVRIQPGQTFSVLACYNGSPSGVYQ

CAMRPNFTIKGSFLNGSCGSVGFNIDYDCV

SFCYMHHMELPTGVHAGTDLEGNFYGPFVDRQTAQAAGTDTTITVNVLA

WLYAAVINGDRWFLNRFTTTLNDFNLVA

MKYNYEPLTQDHVDILGPLSAQTGIAVLDMCASLKELLQNGMNGRTILG

SALLEDEFTPFDVVRQCSGVTFQ
```

A homology model was built from a crystal structure of SARS 3C-like protease in Pfizer's database using Schrödinger's PRIMES. Minimization of the homology model in complex with ligands was used to remove clashes with ligands containing benzothiazole ketones or a benzyl side chains after examining the protein conformations of other SARS 3C-like crystal structures with these ligand moieties. Relaxation of residues in the 185-190 loop, His41 and Met49 to led to three differently minimized versions of the homology model. The catalytic Cys was mutated to Gly (C145G) to facilitate AGDOCK core docking and subsequent scoring without a clash with the catalytic Cys.

Docking: Compounds are docked into the homology models using core docking[4] with AGDOCK[5]. The docking is performed without forming the protein-ligand covalent bond. Instead, a common core that included the lactam side chain and reactive ketone was identified in the ligands and held fixed in the crystal structure orientation as a mimic of covalent docking (See FIG. 2). The affinity measure for AGDOCK core docking is HT Score[6].

METHOD REFERENCES 1. http://www.rcsb.org/structure/3IWM
2. http://www.ncbi.nlm.qov/protein/YP_009725301.1
3. Schrödinger Release 2019-1: Prime, Schrödinger, LLC, New York, N.Y., 2019.
4. Daniel K. Gehlhaar, Gennady M. Verkhivker, Paul A. Rejto, Christopher J. Sherman, David R. Fogel, Lawrence J. Fogel, Stephan T. Freer, Molecular recognition of the inhibitor AG-1343 by HIV-1 protease: conformationally flexible docking by evolutionary programming, Chemistry & Biology, Volume 2, Issue 5, 1995, Pages 317-324.
5. Daniel K. Gehlhaar, Djamal Bouzida, and Paul A. Rejto, Reduced Dimensionality in Ligand -Protein Structure Prediction: Covalent Inhibitors of Serine Proteases and Design of Site-Directed Combinatorial Libraries Rational Drug Design. Jul. 7, 1999, 292-311.
6. Tami J. Marrone, Brock A. Luty, Peter W. Rose, Discovering high-affinity ligands from the computationally predicted structures and affinities of small molecules bound to a target: A virtual screening approach. Perspectives in Drug Discovery and Design 20, 209-230 (2000).

Results:
Homology model: The sequence homology between SARS-CoV and SARS-CoV-2 is 96.1%. There are 12 of 306 residues that are different (T35V, A46S, S65N, L86V, R88K, S94A, H134F, K180N, L202V, A267S, T285A & I286L highlighted in cyan in Figure A) which translates to 96.1% identity.

The ligand associated with the crystal structure used to build the homology model is Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide. The amino acid residue nearest to Compound B, N-((1S)-1-{[((1S)-3-hydroxy-2-oxo {[(3S)-2-oxopyrrolidin-3-yl]methyl}propyl)amino]carbonyl}-3-methylbutyl)-4-methoxy-1H-indole-2-carboxamide, that differed between SARS 3C-like protease and SARS-CoV-2 3C-like protease model is A46S, and the minimum distance from $C_{alpha}$ to ligand is 8.3 Å. Other residues are between 11 Å and 38 Å from the nearest atom in Compound B.

TABLE 1

Approximate distances from $C_{alpha}$ atoms in SARS-CoV-2 to Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide

| SARS-CoV-2 Amino Acid Residues | Distance to Nearest Atom in Compound B (Angstroms) |
| --- | --- |
| T35V | ~19 |
| A46S | ~8 |
| S65N | ~16 |
| L86V | ~11 |
| R88K | ~15 |
| S94A | ~24 |
| H134F | ~14 |
| K180N | ~13 |
| L202V | ~27 |
| A267S | ~38 |
| T285A | ~34 |
| I286L | ~31 |

FIG. 1 depicts the residue differences between SARS-CoV and SARS-CoV-2. Residue changes are highlighted in cyan in this ribbon depiction of SARS-CoV-2 homology model. The Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, location is shown in magenta. The approximate distance between the C-alpha of a SARS-CoV-2 amino acid residue and the closest atom in the Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide, is shown in Table 1, above.

Docking Results:

The approximately 96% homology of SARS-CoV-2 3CL to SARS-CoV 3CL and the similarity between ligands allows a comparison of the RMSD between the peptide backbone of xtal ligand in SARS-CoV (see FIG. 2) and the docked ligand in the SARS-CoV-2 3CL model. The core-docked ligand RMSD to the peptide backbone did not differ by more than 0.32A (average 0.28A). See FIG. 2 for an example. In the case of Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide; the RMSD for the whole molecule was 0.37 A.

Figure 2:
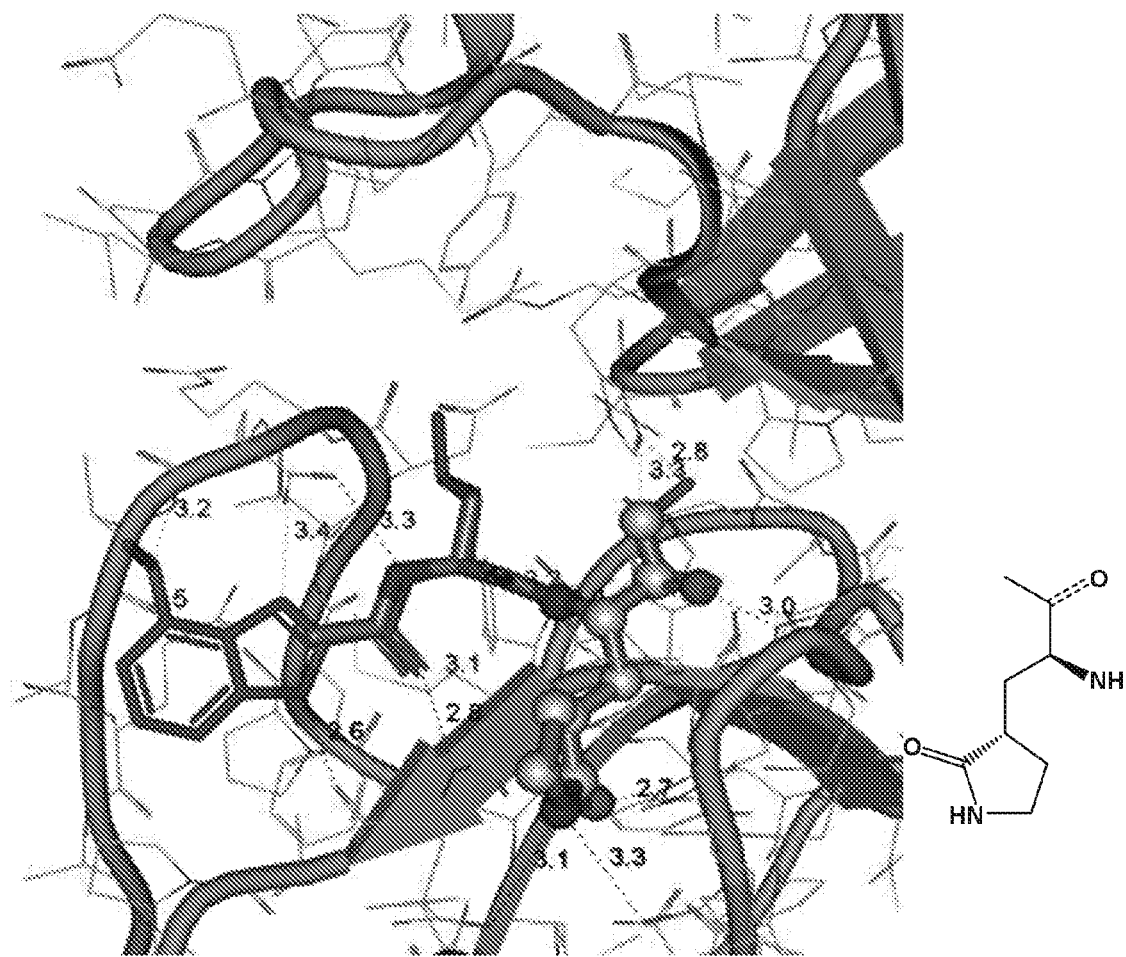
FIG. 2 depicts binding site of homology model of SARS-CoV-2 3CL with a core-docked ligand (Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide).

FIG. 2. Binding site of homology model of SARS-CoV-2 3CL with a core-docked ligand (Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide) present (purple carbons, red oxygen, blue nitrogen). Part of the crystal structure of Compound B, N-((1S)-1-{[((1S)-3-hydroxy-2-oxo-1-{[(3S)-2-oxopyrrolidin-3-yl]methyl}propyl)amino]carbonyl}-3-methylbutyl)-4-methoxy-1H-indole-2-carboxamide; (peptide backbone, lactam side chain and attacked ketone) was used to measure the RMSD of the different ligands to that backbone (grey carbons, thick stick). The core used for core docking is shown as 11 heavy atoms in ball representation (light blue carbons) and in the inset chemical structure. Distances shown in Angstroms.

The docking result(s) in Table 2 below indicate that the compound(s) have predicted affinities ($\Delta G_{bind}$, kcal/mol) that are generally commensurate with target recognition and binding. The effective potency can differ from the $\Delta G$ binding terms depending on several factors such as cell uptake, efflux, cofactor competition or substrate competition.

TABLE 2

| Compound | Predicted $\Delta G_{bind}$ (kcal/mol) | Chemical Name of Docked Compounds |
| --- | --- | --- |
| B | −9.5 | N-((1S)-1-{[((1S)-3-hydroxy-2-oxo-1-{[(3S)-2-oxopyrrolidin-3-yl]methyl}propyl)amino] carbonyl}-3-methylbutyl)-4-methoxy-1H-indole-2-carboxamide |

The compounds described above are analyzed by a FRET biochemical assay and by in vitro virological assays using cell culture techniques.

Protection from SARS Infection: Neutral Red Endpoint

The ability of compounds to protect cells against infection by the SARS coronavirus is measured by a cell viability assay similar to that described in Borenfreund, E., and Puerner, J. 1985. Toxicity determined in vitro by morphological alterations and neutral red absorption Toxicology Letters. 24:119-124, utilizing neutral red staining as an endpoint. Briefly, medium containing appropriate concentrations of compound or medium only is added to Vero cells. Cells are infected with SARS-associated virus or mock-infected with medium only. One to seven days later, the medium is removed and medium containing neutral red is added to the test plates. Following incubation at 37° C. for two hours, cells are washed twice with PBS and a 50% EtOH, 1% acetic acid solution is added. The cells are shaken for 1 to 2 minutes and incubated at 37° C. for 5 to 10 minutes. The amount of neutral red is quantified spectrophotometrically at 540 nm. Data is expressed as the percent of neutral red in wells of compound-treated cells compared to neutral red in wells of uninfected, compound-free cells. The fifty percent effective concentration (EC50) is calculated as the concentration of compound that increases the percent of neutral red production in infected, compound-treated cells to 50% of that produced by uninfected, compound-free cells. The 50% cytotoxicity concentration (CC50) is calculated as the concentration of compound that decreases the percentage of neutral red produced in uninfected, compound-treated cells to 50% of that produced in uninfected, compound-free cells. The therapeutic index is calculated by dividing the cytotoxicity (CC50) by the antiviral activity (EC50).

Protection from SARS-CoV-2 Infection: Glo Endpoint

The ability of compounds to protect cells against infection by the SARS-CoV-2 coronavirus can also be measured by a cell viability assay utilizing luciferase to measure intracellular ATP as an endpoint. Briefly, medium containing appropriate concentrations of compound or medium only is added to Vero cells. Cells are infected with SARS-CoV-2 virus or mock-infected with medium only. One to seven days later, the medium is removed and the amount of intracellular ATP is measured as per Promega Technical Bulletin No. 288: CellTiter-Glo® Luminescent Cell Viability Assay (Promega, Madison, WI). The CellTiter-Glo® reagent is added to the test plates and following incubation at 37° C. for 1.25 hours, the amount of signal is quantified using a luminometer at 490 nm. Data is expressed as the percent of luminescent signal from wells of compound-treated cells compared to the luminescent signal from wells of uninfected, compound-free cells. The fifty percent effective concentration (EC50) is calculated as the concentration of compound that increases the percent of the luminescent signal from infected, compound-treated cells to 50% of the luminescent signal from uninfected, compound-free cells. The 50% cytotoxicity concentration (CC50) is calculated as the concentration of compound that decreases the percentage of the luminescent signal from uninfected, compound-treated cells to 50% of the luminescent signal from uninfected, compound-free cells. The therapeutic index is calculated by dividing the cytotoxicity (CC50) by the antiviral activity (EC50).

Cytotoxicity

The ability of compounds to cause cytotoxicity in cells is measured by a cell viability assay similar to that described in Weislow, O. S., Kiser, R., Fine, D. L., Bader, J., Shoemaker, R. H., and Boyd, M. R. 1989. New Soluble-Formazan Assay for HIV-1 Cytopathic Effects: Application to High-Flux Screening of Synthetic and Natural Products for AIDS-Antiviral Activity. Journal of the National Cancer Institute 81(08): 577-586, utilizing formazan as an endpoint. Briefly, Vero cells are resuspended in medium containing appropriate concentrations of compound or medium only. One to seven days later, XTT and PMS are added to the test plates and following incubation at 37° C. for two hours the amount of formazan produced is quantified spectrophotometrically at 540 nm. Data is expressed as the percent of formazan produced in compound-treated cells compared to formazan produced in wells of compound-free cells. The 50% cytotoxicity concentration (CC50) is calculated as the concentration of compound that decreases the percentage of formazan produced in uninfected, compound-treated cells to 50% of that produced in uninfected, compound-free cells.

Protection from SARS-CoV-2 Coronavirus Infection

The ability of compounds to protect cells against infection by SARS-CoV-2 is measured by a cell viability assay similar to that described in Weislow, O. S., Kiser, R., Fine, D. L., Bader, J., Shoemaker, R. H., and Boyd, M. R. 1989. New Soluble-Formazan Assay for HIV-1 Cytopathic Effects: Application to High-Flux Screening of Synthetic and Natural Products for AIDS-Antiviral Activity. Journal of the National Cancer Institute 81(08): 577-586, utilizing formazan as an endpoint. Briefly, medium containing appropriate concentrations of compound or medium only is added to MRC-5 cells. Cells are infected with human coronavirus SARS-CoV-2 or mock-infected with medium only. One to seven days later, XTI and PMS are added to the test plates and following incubation at 37° C. for two hours the amount of formazan produced is quantified spectrophotometrically at 540 nm. Data is expressed as the percent of formazan in wells of compound-treated cells compared to formazan in wells of uninfected, compound-free cells. The fifty percent effective concentration (EC50) is calculated as the concentration of compound that increases the percent of formazan production in infected, compound-treated cells to 50% of that produced by uninfected, compound-free cells. The 50% cytotoxicity concentration (CC50) is calculated as the concentration of compound that decreases the percentage of formazan produced in uninfected, compound-treated cells to 50% of that produced in uninfected, compound-free cells. The therapeutic index is calculated by dividing the cytotoxicity (CC50) by the antiviral activity (EC50).

SARS-CoV-2 Coronavirus 3C Protease FRET Assay and Analysis

Proteolytic activity of SARS-CoV-2 Coronavirus 3CL protease is measured using a continuous fluorescence resonance energy transfer assay. The SARS-CoV-2 $3CL^{pro}$ FRET assay measures the protease catalyzed cleavage of TAMRA-SIT-SAVLQSGFRKMK-(DABCYL)-OH to TAMRA-SIT-SAVLQ and SGFRKMK(DABCYL)-OH. The fluorescence of the cleaved TAMRA (ex. 558 nm/em. 581 nm) peptide was measured using a TECAN SAFI RE fluorescence plate reader over the course of 10 min. Typical reaction solutions contained 20 mM HEPES (pH 7.0), 1 mM EDTA, 4.0 uM FRET substrate, 4% DMSO and 0.005% Tween-20. Assays were initiated with the addition of 25 nM SARS $3CL^{pro}$ (nucleotide sequence 9985-10902 of the Urbani strain of SARS coronavirus complete genome sequence (NCBI accession number AY278741)). Percent inhibition was determined in duplicate at 0.001 mM level of inhibitor. Data was analyzed with the non-linear regression analysis program Kalidagraph using the equation:

$$FU = \text{offset} + (\text{limit})(1 - e^{-(k_{obs})t})$$

where offset equals the fluorescence signal of the uncleaved peptide substrate, and limit equals the fluorescence of fully cleaved peptide substrate. The kobs is the first order rate constant for this reaction, and in the absence of any inhibitor represents the utilization of substrate. In an enzyme start reaction which contains an irreversible inhibitors, and where the calculated limit is less than 20% of the theoretical maximum limit, the calculated kobs represents the rate of inactivation of coronavirus 3C protease. The slope (kobs/I) of a plot of kobs vs. [I] is a measure of the avidity of the inhibitor for an enzyme. For very fast irreversible inhibitors, kobs/I is calculated from observations at only one or two [I] rather than as a slope.

Alternatively the antiviral activity of the compounds, as reported in Table 3, can be assessed using the following assay conditions:

Antiviral Activity from SARS-CoV-2 Infection

The ability of compounds to prevent SARS-CoV-2 coronavirus-induced cell death or cytopathic effect can be assessed via cell viability, using an assay format that utilizes luciferase to measure intracellular ATP as an endpoint. In brief, VeroE6 cells that are enriched for hACE2 expression were batched inoculated with SARS-CoV-2 (USA_WA1/2020) at a multiplicity of infection of 0.002 in a BSL-3 lab. Virus-inoculated cells were then added to assay-ready compound plates at a density of 4,000 cells/well. Following a 3-day incubation, a time at which virus-induced cytopathic effect is 95% in the untreated, infected control conditions, cell viability was evaluated using Cell Titer-Glo (Promega), according to the manufacturer's protocol, which quantitates ATP levels. Cytotoxicity of the compounds was assessed in parallel non-infected cells. Test compounds are tested either alone or in the presence of the P-glycoprotein (P-gp) inhibitor CP-100356 at a concentration of 2 µM. The inclusion of CP-100356 is to assess if the test compounds are being effluxed out of the VeroE6 cells, which have high levels of expression of P-glycoprotein. Percent effect at each concentration of test compound was calculated based on the values for the no virus control wells and virus-containing control wells on each assay plate. The concentration required for a 50% response (EC50) value was determined from these data using a 4-parameter logistic model. EC50 curves were fit to a Hill slope of 3 when >3 and the top dose achieved 50% effect. If cytotoxicity was detected at greater than 30% effect, the corresponding concentration data was eliminated from the EC50 determination.

For cytotoxicity plates, a percent effect at each concentration of test compound was calculated based on the values for the cell-only control wells and hyamine-containing control wells on each assay plate. The 0050 value was calculated using a 4-parameter logistic model. A TI was then calculated by dividing the 0050 value by the EC50 value.

SARS-CoV-2 Coronavirus 3C Protease FRET Assay and Analysis

The proteolytic activity of the main protease, 3CLpro, of SARS-CoV-2 was monitored using a continuous fluorescence resonance energy transfer (FRET) assay. The SARS-CoV-2 3CLpro assay measures the activity of full-length SARS-CoV-2 3CL protease to cleave a synthetic fluorogenic substrate peptide with the following sequence: Dabcyl-KTSAVLQ-SGFRKME-Edans modelled on a consensus peptide (V. Grum-Tokars et al. Evaluating the 3C-like protease activity of SARS-coronavirus: recommendations for standardized assays for drug discovery. Virus Research 133 (2008) 63-73). The fluorescence of the cleaved Edans peptide (excitation 340 nm/emission 490 nm) is measured using a fluorescence intensity protocol on a Flexstation reader (Molecular Devices). The fluorescent signal is reduced in the present of PF-835231, a potent inhibitor of SARS-CoV-2 3CLpro. The assay reaction buffer contained 20 mM Tris-HCl (pH 7.3), 100 nM NaCl, 1 mM EDTA and 25 µM peptide substrate. Enzyme reactions were initiated with the addition of 15 nM SARS-CoV-2 3CL protease and allowed to proceed for 60 minutes at 23° C. Percent inhibition or activity was calculated based on control wells containing no compound (0% inhibition/100% activity) and a control compound (100% inhibition/0% activity). $IC_{50}$ values were generated using a four-parameter fit model using ABASE software (IDBS). Ki values were fit to the Morrison equation with the enzyme concentration parameter fixed to 15 nM, the Km parameter fixed to 14 μM and the substrate concentration parameter fixed to 25 μM using ABASE software (IDBS).

Proteolytic activity of SARS-CoV-2 Coronavirus 3CL protease is measured using a continuous fluorescence resonance energy transfer assay. The SARS-CoV-2 3CL$^{pro}$ FRET assay measures the protease catalyzed cleavage of TAMRA-SITSAVLQSGFRKMK-(DABCYL)-OH to TAMRA-SITSAVLQ and SGFRKMK(DABCYL)-OH. The fluorescence of the cleaved TAMRA (ex. 558 nm/em. 581 nm) peptide was measured using a TECAN SAFI RE fluorescence plate reader over the course of 10 min. Typical reaction solutions contained 20 mM HEPES (pH 7.0), 1 mM EDTA, 4.0 μM FRET substrate, 4% DMSO and 0.005% Tween-20. Assays were initiated with the addition of 25 nM SARS 3CL$^{pro}$ (nucleotide sequence 9985-10902 of the Urbani strain of SARS coronavirus complete genome sequence (NCBI accession number AY278741)). Percent inhibition was determined in duplicate at 0.001 mM level of inhibitor. Data was analyzed with the non-linear regression analysis program Kalidagraph using the equation:

$$FU = \text{offset} + (\text{limit})(1 - e^{-(kobs)t})$$

where offset equals the fluorescence signal of the un-cleaved peptide substrate, and limit equals the fluorescence of fully cleaved peptide substrate. The kobs is the first order rate constant for this reaction, and in the absence of any inhibitor represents the utilization of substrate. In an enzyme start reaction which contains an irreversible inhibitor, and where the calculated limit is less than 20% of the theoretical maximum limit, the calculated kobs represents the rate of inactivation of coronavirus 3C protease. The slope (kobs/I) of a plot of kobs vs. [I] is a measure of the avidity of the inhibitor for an enzyme. For very fast irreversible inhibitors, kobs/I is calculated from observations at only one or two [I] rather than as a slope.

TABLE 3

Biological activity for selected Examples

| Example Number | Geometric Mean K$_i$ (nM) | Count Used K$_i$ (nM) | Geometric Mean EC$_{50}$ (nM) | Count Used EC$_{50}$ (nM) |
|---|---|---|---|---|
| 4 | 2.98 | 2 | N.D.[1] | |
| 9 | 33.6 | 2 | N.D. | |
| 10 | 63.7 | 2 | 205 | 2 |
| 11 | 71.4 | 2 | N.D. | |
| 12 | 73.8 | 2 | 109 | 4 |

TABLE 3-continued

Biological activity for selected Examples

| Example Number | Geometric Mean K$_i$ (nM) | Count Used K$_i$ (nM) | Geometric Mean EC$_{50}$ (nM) | Count Used EC$_{50}$ (nM) |
|---|---|---|---|---|
| 13 | 139 | 2 | N.D. | |
| 14 | 348 | 2 | 505 | 2 |
| 15 | 147 | 2 | N.D. | |
| 16 | 10.5 | 2 | N.D. | |
| 17 | 17.5 | 2 | N.D. | |
| 18 | 65.7 | 2 | N.D. | |
| 19 | 64.8 | 1 | N.D. | |
| 21 | 104 | 2 | N.D. | |
| 23 | 21.2 | 2 | N.D. | |
| 24 | 14.2 | 2 | N.D. | |
| 27 | 0.0321 | 5 | N.D. | |
| 28 | 2.47 | 3 | N.D. | |
| 29 | 9.57 | 3 | N.D. | |
| 30 | 6.13 | 3 | N.D. | |
| 34 | 0.598 | 5 | N.D. | |
| 35 | 4.43 | 3 | N.D. | |
| 37 | 1.42 | 3 | N.D. | |
| 39 | 91.9 | 2 | N.D. | |
| 40 | 306 | 2 | N.D. | |
| 42 | 5.25 | 3 | N.D. | |
| 43 | 118 | 1 | N.D. | |
| 44 | 90.6 | 2 | N.D. | |
| 45 | 40.7 | 2 | N.D. | |
| 48 | 255 | 2 | N.D. | |
| 51 | 152 | 2 | N.D. | |
| 53 | 14 | 2 | 538 | 2 |
| 59 | 13.6 | 2 | N.D. | |
| 62 | 4.29 | 2 | N.D. | |
| 64 | 34.9 | 2 | N.D. | |
| 65 | 7.67 | 2 | 51.3 | 4 |
| 66 | 39.6 | 2 | N.D. | |
| 67 | 8.82 | 2 | 163 | 4 |
| 68 | 7.56 | 2 | N.D. | |
| 69 | N.D. | | N.D. | |
| 70 | 5.89 | 3 | 4800 | 2 |
| 71 | 0.928 | 3 | 315 | 6 |
| 72 | 8.91 | 2 | N.D. | |
| 73 | 117 | 2 | N.D. | |
| 74 | 44.3 | 2 | N.D. | |
| 75 | 5.50 | 2 | N.D. | |

[1]N.D.—Not determined

All patents and publications described hereinabove are hereby incorporated by reference in their entirety. While the invention has been described in terms of various preferred embodiments and specific examples, the invention should be understood as not being limited by the foregoing detailed description, but as being defined by the appended claims and their equivalents.

What is claimed is:

1. A compound of Formula I

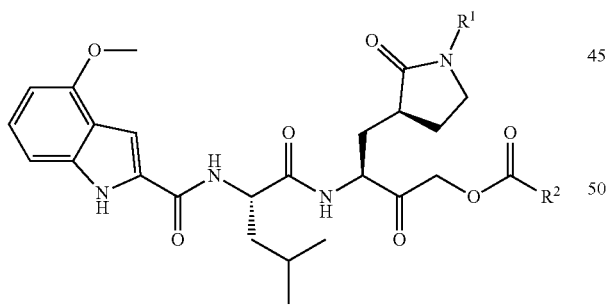

wherein $R^1$ is selected from the group consisting of hydrogen, -C(O)C$_1$-C$_6$alkyl, -C(O)OC$_1$-C$_6$alkyl and -C$_1$-C$_6$alkylOC(O)OC$_1$-C$_6$alkyl;

when $R^1$ is hydrogen then $R^2$ is selected from the group consisting of ethyl, isopropyl, 2-methylpropyl, C$_1$-C$_6$alkyl substituted with one to three $R^3$, cyclopropyl substituted with one to three $R^4$, C$_4$-C$_7$cycloalkyl unsubstituted or substituted with one to three $R^4$, C$_5$-C$_{12}$bicycloalkyl unsubstituted or substituted with one to three $R^4$, four- to seven-membered heterocycloalkyl comprising one to three heteroatoms selected independently from N, O and S and which is unsubstituted or substituted with one to three $R^4$, five- to ten-membered heteroaryl comprising one to four heteroatoms selected independently from N, O and S and which is unsubstituted or substituted with one to three $R^4$, 2-methylphenyl, 2-methoxyphenyl, 2-chlorophenyl, 2-methoxymethylphenyl, 2-(dimethylamino)methylphenyl, 2-(dimethylamino)methyl-6-methylphenyl, 2-methoxymethyl-6-methylphenyl, 4-cyano-2,6-dimethylphenyl, 2-methoxy-6-methylphenyl, 2-fluoro-6-methylphenyl, 2-chloro-6-methylphenyl, 4-chloro-2,6-dimethylphenyl, 2,6-dimethyl-4-methoxyphenyl, 2,6-dimethyl-4-fluorophenyl and 2,6-dimethyl-3-fluorophenyl;

when $R^1$ is -C(O) C$_1$-C$_6$alkyl, -C(O)OC$_1$-C$_6$alkyl or -C$_1$-C$_6$alkylOC(O)OC$_1$-C$_6$alkyl then $R^2$ is selected from the group consisting of C$_1$-C$_6$alkyl unsubstituted or substituted with one to three $R^3$, C$_3$-C$_7$cycloalkyl unsubstituted or substituted with one to three $R^4$, C$_5$-C$_{12}$bicycloalkyl unsubstituted or substituted with one to three $R^4$, four-to seven-membered heterocycloalkyl comprising one to three heteroatoms selected independently from N, O and S and which is unsubstituted or substituted with one to three $R^4$, C$_6$-C$_{10}$aryl unsubstituted or substituted with one to three $R^4$, and five-to ten-membered heteroaryl comprising one to four heteroatoms selected independently from N, O and S and which is unsubstituted or substituted with one to three $R^4$;

R³ at each occurrence is independently selected from the group consisting of halo, cyano, hydroxy, di($C_1$-$C_6$alkyl)amino, ($C_1$-$C_6$alkyl)amino and amino; and R⁴ at each occurrence is independently selected from halo, hydroxy, cyano, $C_1$-$C_3$alkyl, $C_1$-$C_3$alkoxy, $C_1$-$C_3$alkoxy$C_1$-$C_3$alkyl, di($C_1$-$C_3$alkyl)amino, ($C_1$-$C_3$alkyl)amino, amino, di($C_1$-$C_3$alkyl)amino-$C_1$-$C_3$alkyl, ($C_1$-$C_3$alkyl)amino-$C_1$-$C_3$alkyl, amino-$C_1$-$C_3$alkyl and four-to seven-membered heterocycloalkyl comprising one to three heteroatoms selected independently from N, O and S;

or a pharmaceutically acceptable salt thereof.

2. The compound of claim 1 wherein R¹ is hydrogen; or a pharmaceutically acceptable salt thereof.

3. The compound of claim 2 wherein R² is selected from the group consisting of ethyl, isopropyl, 2-methylpropyl, $C_1$-$C_6$alkyl substituted with one to three R³, cyclopropyl substituted with one to three R⁴, $C_4$-$C_7$cycloalkyl unsubstituted or substituted with one to three R⁴, and $C_5$-$C_{12}$bicycloalkyl unsubstituted or substituted with one to three R⁴; or a pharmaceutically acceptable salt thereof.

4. The compound of claim 3 selected from the group consisting of:
   (3S)-3-({N-[(4-methoxy-1H-indol-2-yl) carbonyl]-L-leucyl}amino)-2-oxo-4-[(3S)-2-oxopyrrolidin-3-yl]butyl N,N-dimethylglycinate;
   (3S)-3-({N-[(4-methoxy-1H-indol-2-yl) carbonyl]-L-leucyl}amino)-2-oxo-4-[(3S)-2-oxopyrrolidin-3-yl]butyl N,N-dimethyl-D-alaninate;
   (3S)-3-({N-[(4-methoxy-1H-indol-2-yl) carbonyl]-L-leucyl}amino)-2-oxo-4-[(3S)-2-oxopyrrolidin-3-yl]butyl N,N,2-trimethylalaninate;
   (3S)-3-({N-[(4-methoxy-1H-indol-2-yl) carbonyl]-L-leucyl}amino)-2-oxo-4-[(3S)-2-oxopyrrolidin-3-yl]butyl 4-(dimethylamino)-2,2-dimethylbutanoate;
   (3S)-3-({N-[(4-methoxy-1H-indol-2-yl) carbonyl]-L-leucyl}amino)-2-oxo-4-[(3S)-2-oxopyrrolidin-3-yl]butyl 4-(dimethylamino) butanoate;
   (3S)-3-({N-[(4-methoxy-1H-indol-2-yl) carbonyl]-L-leucyl}amino)-2-oxo-4-[(3S)-2-oxopyrrolidin-3-yl]butyl propanoate (3S)-3-({N-[(4-methoxy-1H-indol-2-yl) carbonyl]-L-leucyl}amino)-2-oxo-4-[(3S)-2-oxopyrrolidin-3-yl]butyl 2-methylpropanoate;
   (3S)-3-({N-[(4-methoxy-1H-indol-2-yl) carbonyl]-L-leucyl}amino)-2-oxo-4-[(3S)-2-oxopyrrolidin-3-yl]butyl cyclohexanecarboxylate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methylcyclohexanecarboxylate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methylcyclobutanecarboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (2S)-2-methylbutanoate;
   (3S)-3-({N-[(4-methoxy-1H-indol-2-yl) carbonyl]-L-leucyl}amino)-2-oxo-4-[(3S)-2-oxopyrrolidin-3-yl]butyl (2R)-2-methylbutanoate;
   (3S)-3-({N-[(4-methoxy-1H-indol-2-yl) carbonyl]-L-leucyl}amino)-2-oxo-4-[(3S)-2-oxopyrrolidin-3-yl]butyl bicyclo[1.1.1]pentane-1-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methylcyclopropanecarboxylate; and
   (3S)-3-({N-[(4-methoxy-1H-indol-2-yl) carbonyl]-L-leucyl}amino)-2-oxo-4-[(3S)-2-oxopyrrolidin-3-yl]butyl L-valinate;

or a pharmaceutically acceptable salt thereof.

5. The compound of claim 1 wherein R² is a four-to seven-membered heterocycloalkyl comprising one to three heteroatoms selected independently from N, O and S and which is unsubstituted or substituted with one to three R⁴; or a pharmaceutically acceptable salt thereof.

6. The compound of claim 5 wherein R² is selected from the group consisting of azetidinyl, pyrrolidinyl, piperidinyl and morpholinyl; each of which is unsubstituted or substituted with one to two R⁴; or a pharmaceutically acceptable salt thereof.

7. The compound of claim 6 wherein R² is selected from the group consisting of azetidinyl, pyrrolidinyl, piperidinyl and morpholinyl; each of which is substituted with one to two methyl; or a pharmaceutically acceptable salt thereof.

8. The compound of claim 1 which is selected from the group consisting of:
   (3S)-3-({N-[(4-methoxy-1H-indol-2-yl) carbonyl]-L-leucyl}amino)-2-oxo-4-[(3S)-2-oxopyrrolidin-3-yl]butyl 1,4-dimethylpiperidine-4-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl 1,3-dimethylazetidine-3-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (3R)-1-methylpyrrolidine-3-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (3S)-1-methylpyrrolidine-3-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methyl-D-prolinate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methyl-L-prolinate;
   (3S)-3-({N-[(4-methoxy-1H-indol-2-yl) carbonyl]-L-leucyl}amino)-2-oxo-4-[(3S)-2-oxopyrrolidin-3-yl]butyl 1-methylpiperidine-4-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (2R)-4-methylmorpholine-2-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (2S)-1-methylpiperidine-2-carboxylate;
   (3S)-3-({N-[(4-methoxy-1H-indol-2-yl) carbonyl]-L-leucyl}amino)-2-oxo-4-[(3S)-2-oxopyrrolidin-3-yl]butyl (2S)-4-methylmorpholine-2-carboxylate; and
   (3S)-3-({N-[(4-methoxy-1H-indol-2-yl) carbonyl]-L-leucyl}amino)-2-oxo-4-[(3S)-2-oxopyrrolidin-3-yl]butyl (2R)-1-methylpiperidine-2-carboxylate;

or a pharmaceutically acceptable salt thereof.

9. The compound of claim 1 wherein R² is a five-to ten-membered heteroaryl comprising one to four heteroatoms selected independently from N, O and S and which is unsubstituted or substituted with one to three R⁴; or a pharmaceutically acceptable salt thereof.

10. The compound of claim 9 wherein R² is an imidazolyl, pyrazolyl, isoxazolyl, pyridinyl or pyrimidinyl, each of which is unsubstituted or substituted with one to three R⁴; or a pharmaceutically acceptable salt thereof.

11. The compound of claim 10 wherein R⁴ at each occurrence is independently selected from methyl, methoxy, ethoxy, methoxymethyl, methylamino, (dimethylamino)methyl and tetrahydropyranyl; or a pharmaceutically acceptable salt thereof.

12. The compound of claim 1 selected from the group consisting of:

(3S)-3-({N-[(4-methoxy-1H-indol-2-yl) carbonyl]-L-leucyl}amino)-2-oxo-4-[(3S)-2-oxopyrrolidin-3-yl]butyl 4-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl pyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl pyridine-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl pyridine-2-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1,3-dimethyl-1H-pyrazole-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1,5-dimethyl-1H-imidazole-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-pyrazole-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-pyrazole-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-pyrazole-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-imidazole-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-imidazole-2-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-methoxy-1-methyl-1H-imidazole-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1,3,5-trimethyl-1H-pyrazole-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1,4-dimethyl-1H-pyrazole-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1,4-dimethyl-1H-pyrazole-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 1-methyl-1H-imidazole-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2-(methoxymethyl)-4-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-(methoxymethyl)-6-methylpyrimidine-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-(methoxymethyl)-2-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2-[(dimethylamino)methyl]-4-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-[(dimethylamino)methyl]-6-methylpyrimidine-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-[(dimethylamino)methyl]-2-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2,4-dimethylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4-methyl-2-(methylamino)pyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2-ethoxy-4-methylpyridine-3-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 3,5-dimethylpyridine-4-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 2,4,6-trimethylpyrimidine-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4,6-dimethylpyrimidine-5-carboxylate;

(3S)-3-({N-[(4-methoxy-1H-indol-2-yl) carbonyl]-L-leucyl}amino)-2-oxo-4-[(3S)-2-oxopyrrolidin-3-yl]butyl 4,6-dimethyl-2-(tetrahydro-2H-pyran-4-yl)pyrimidine-5-carboxylate; and (3S)-3-({N-[(4-methoxy-1H-indol-2-yl) carbonyl]-L-leucyl}amino)-2-oxo-4-[(3S)-2-oxopyrrolidin-3-yl]butyl 3,5-dimethyl-1,2-oxazole-4-carboxylate;

or a pharmaceutically acceptable salt thereof.

13. The compound of claim 2 selected from the group consisting of:

(3S)-3-({N-[(4-methoxy-1H-indol-2-yl) carbonyl]-L-leucyl}amino)-2-oxo-4-[(3S)-2-oxopyrrolidin-3-yl]butyl 2-methylbenzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-methoxybenzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-chlorobenzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-(methoxymethyl)benzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-[(dimethylamino)methyl]benzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-[(dimethylamino)methyl]-6-methylbenzoate;

(3S)-3-({N-[(4-methoxy-1H-indol-2-yl) carbonyl]-L-leucyl}amino)-2-oxo-4-[(3S)-2-oxopyrrolidin-3-yl]butyl 2-(methoxymethyl)-6-methylbenzoate;

(3S)-3-({N-[(4-methoxy-1H-indol-2-yl) carbonyl]-L-leucyl}amino)-2-oxo-4-[(3S)-2-oxopyrrolidin-3-yl]butyl 4-cyano-2,6-dimethylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 2-methoxy-6-methylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 2-chloro-6-methylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 4-chloro-2,6-dimethylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 2-fluoro-6-methylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 4-methoxy-2,6-dimethylbenzoate;
(3S)-3-({N-[(4-methoxy-1H-indol-2-yl) carbonyl]-L-leucyl}amino)-2-oxo-4-[(3S)-2-oxopyrrolidin-3-yl]butyl 4-fluoro-2,6-dimethylbenzoate; and
(3S)-3-({N-[(4-methoxy-1H-indol-2-yl) carbonyl]-L-leucyl}amino)-2-oxo-4-[(3S)-2-oxopyrrolidin-3-yl]butyl 3-fluoro-2,6-dimethylbenzoate;
or a pharmaceutically acceptable salt thereof.

14. The compound of claim 1 wherein $R^1$ is -C(O)$C_1$-$C_6$alkyl, -C(O)O$C_1$-$C_6$alkyl and -$C_1$-$C_6$alkylOC (O) O$C_1$-$C_6$alkyl; or a pharmaceutically acceptable salt thereof.

15. The compound of claim 14 wherein $R^1$ is -C(O)CH$_3$, -C(O)OCH$_3$ or -CH(CH$_3$)OC(O)OCH$_3$; or a pharmaceutically acceptable salt thereof.

16. The compound of claim 14 wherein $R^2$ is a $C_6$-$C_{10}$aryl which is unsubstituted or substituted with one to three $R^4$; or a pharmaceutically acceptable salt thereof.

17. The compound of claim 16 wherein $R^2$ is phenyl which is unsubstituted or substituted with one to three $R^4$; or a pharmaceutically acceptable salt thereof.

18. The compound of claim 17 wherein $R^2$ is 2,6-dimethylphenyl; or a pharmaceutically acceptable salt thereof.

19. The compound of claim 18 selected from the group consisting of:
(3S)-4-[(3S)-1-acetyl-2-oxopyrrolidin-3-yl]-3-({N-[(4-methoxy-1H-indol-2-yl) carbonyl]-L-leucyl}amino)-2-oxobutyl 2,6-dimethylbenzoate;
methyl (3S)-3-[(2S)-4-[(2,6-dimethylbenzoyl)oxy]-2-({N-[(4-methoxy-1H-indol-2-yl) carbonyl]-L-leucyl}amino)-3-oxobutyl]-2-oxopyrrolidine-1-carboxylate; and
(3S)-4-[(3S)-1-{(1S)-1-[(methoxycarbonyl)oxy]ethyl}-2-oxopyrrolidin-3-yl]-3-({N-[(4-methoxy-1H-indol-2-yl) carbonyl]-L-leucyl}amino)-2-oxobutyl 2,6-dimethylbenzoate;
or a pharmaceutically acceptable salt thereof.

20. A pharmaceutical composition comprising a therapeutically effective amount of a compound of claim 1 or a pharmaceutically acceptable salt thereof together with a pharmaceutically acceptable carrier.

21. The pharmaceutical composition of claim 20 further comprising one or more additional therapeutic agents.

22. The pharmaceutical composition of claim 21 wherein the additional therapeutic agent is selected from azithromycin and remdesivir.

23. A method of treating COVID-19 in a patient, the method comprising administering a therapeutically effective amount of a compound of claim 1 or a pharmaceutically acceptable salt thereof to a patient in need thereof.

* * * * *

SEQUENCE LISTING

<160> NUMBER OF SEQ ID NOS: 2

<210> SEQ ID NO 1
<211> LENGTH: 306
<212> TYPE: PRT
<213> ORGANISM: Homo sapiens

<400> SEQUENCE: 1

Ser Gly Phe Arg Lys Met Ala Phe Pro Ser Gly Lys Val Glu Gly Cys
1               5                   10                  15

Met Val Gln Val Thr Cys Gly Thr Thr Thr Leu Asn Gly Leu Trp Leu
            20                  25                  30

Asp Asp Val Val Tyr Cys Pro Arg His Val Ile Cys Thr Ser Glu Asp

```
                35                  40                  45
Met Leu Asn Pro Asn Tyr Glu Asp Leu Leu Ile Arg Lys Ser Asn His
 50                  55                  60

Asn Phe Leu Val Gln Ala Gly Asn Val Gln Leu Arg Val Ile Gly His
 65                  70                  75                  80

Ser Met Gln Asn Cys Val Leu Lys Leu Lys Val Asp Thr Ala Asn Pro
                 85                  90                  95

Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
        115                 120                 125

Ala Met Arg Pro Asn Phe Thr Ile Lys Gly Ser Phe Leu Asn Gly Ser
    130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
        195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
                245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
        275                 280                 285

Asp Glu Phe Thr Pro Phe Asp Val Val Arg Gln Cys Ser Gly Val Thr
    290                 295                 300

Phe Gln
305

<210> SEQ ID NO 2
<211> LENGTH: 306
<212> TYPE: PRT
<213> ORGANISM: Homo sapiens

<400> SEQUENCE: 2

Ser Gly Phe Arg Lys Met Ala Phe Pro Ser Gly Lys Val Glu Gly Cys
 1               5                  10                  15

Met Val Gln Val Thr Cys Gly Thr Thr Thr Leu Asn Gly Leu Trp Leu
                 20                  25                  30

Asp Asp Val Val Tyr Cys Pro Arg His Val Ile Cys Thr Ser Glu Asp
            35                  40                  45

Met Leu Asn Pro Asn Tyr Glu Asp Leu Leu Ile Arg Lys Ser Asn His
 50                  55                  60

Asn Phe Leu Val Gln Ala Gly Asn Val Gln Leu Arg Val Ile Gly His
 65                  70                  75                  80

Ser Met Gln Asn Cys Val Leu Lys Leu Lys Val Asp Thr Ala Asn Pro
                 85                  90                  95
```

```
Lys Thr Pro Lys Tyr Lys Phe Val Arg Ile Gln Pro Gly Gln Thr Phe
            100                 105                 110

Ser Val Leu Ala Cys Tyr Asn Gly Ser Pro Ser Gly Val Tyr Gln Cys
            115                 120                 125

Ala Met Arg Pro Asn Phe Thr Ile Lys Gly Ser Phe Leu Asn Gly Ser
            130                 135                 140

Cys Gly Ser Val Gly Phe Asn Ile Asp Tyr Asp Cys Val Ser Phe Cys
145                 150                 155                 160

Tyr Met His His Met Glu Leu Pro Thr Gly Val His Ala Gly Thr Asp
                165                 170                 175

Leu Glu Gly Asn Phe Tyr Gly Pro Phe Val Asp Arg Gln Thr Ala Gln
            180                 185                 190

Ala Ala Gly Thr Asp Thr Thr Ile Thr Val Asn Val Leu Ala Trp Leu
            195                 200                 205

Tyr Ala Ala Val Ile Asn Gly Asp Arg Trp Phe Leu Asn Arg Phe Thr
    210                 215                 220

Thr Thr Leu Asn Asp Phe Asn Leu Val Ala Met Lys Tyr Asn Tyr Glu
225                 230                 235                 240

Pro Leu Thr Gln Asp His Val Asp Ile Leu Gly Pro Leu Ser Ala Gln
            245                 250                 255

Thr Gly Ile Ala Val Leu Asp Met Cys Ala Ser Leu Lys Glu Leu Leu
            260                 265                 270

Gln Asn Gly Met Asn Gly Arg Thr Ile Leu Gly Ser Ala Leu Leu Glu
            275                 280                 285

Asp Glu Phe Thr Pro Phe Asp Val Val Arg Gln Cys Ser Gly Val Thr
            290                 295                 300

Phe Gln
305
```